(12) United States Patent
Jolidon et al.

(10) Patent No.: US 7,241,761 B2
(45) Date of Patent: Jul. 10, 2007

(54) PHENYL-PIPERAZINE METHANONE DERIVATIVES, SUBSTITUTED BY HETEROCYCLIC GROUPS

(75) Inventors: Synese Jolidon, Blauen (CH); Robert Narquizian, St. Louis (FR); Roger David Norcross, Olsberg (CH); Emmanuel Pinard, Linsdorf (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/291,216

(22) Filed: Dec. 1, 2005

(65) Prior Publication Data
US 2006/0128712 A1 Jun. 15, 2006

(30) Foreign Application Priority Data
Dec. 9, 2004 (EP) .................................. 04106440

(51) Int. Cl.
*A61K 31/496* (2006.01)
*A61K 31/5377* (2006.01)
*C07D 413/04* (2006.01)
*C07D 417/04* (2006.01)
*C07D 417/14* (2006.01)
*A61K 31/498* (2006.01)
*C07D 401/04* (2006.01)
*C07D 403/04* (2006.01)

(52) U.S. Cl. .................. 514/235.8; 514/254.02; 514/254.04; 514/249; 514/253.06; 544/121; 544/368; 544/356; 544/360; 544/364

(58) Field of Classification Search ............... 544/368, 544/121
See application file for complete search history.

(56) References Cited
U.S. PATENT DOCUMENTS

| 3,933,802 | A | 1/1976 | Ferrini et al. |
| 4,244,871 | A | 1/1981 | Kosary et al. |
| 2005/0059668 | A1 | 3/2005 | Alberati-Giani et al. |
| 2005/0070539 | A1 | 3/2005 | Alberati-Giani et al. |
| 2005/0209241 | A1 | 9/2005 | Jolidon et al. |

FOREIGN PATENT DOCUMENTS

| EP | 0 171 636 | 2/1985 |
| EP | 0 624 584 | 11/1994 |
| FR | 2 861 073 A1 | 4/2005 |

(Continued)

OTHER PUBLICATIONS

Lewis D.A. & Lieberman J.A., Neuron. vol. 28, pp. 325-334 (2000).

(Continued)

Primary Examiner—Emily Bernhardt

(74) Attorney, Agent, or Firm—George W. Johnston; Patricia S. Rocha-Tramaloni; Kimberly J. Prior

(57) ABSTRACT

The present invention relates to compounds of the general formula I

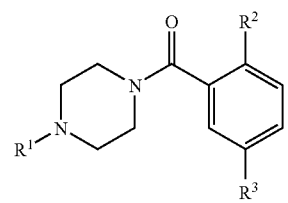

I wherein
$R^1$ is the group

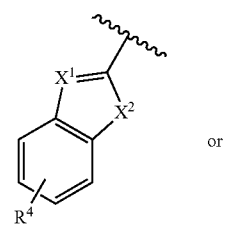

A or

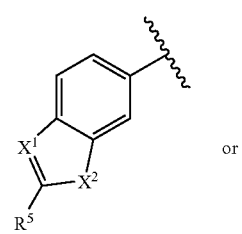

B or

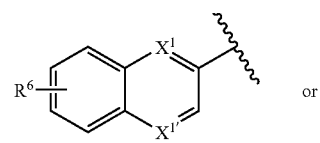

C or

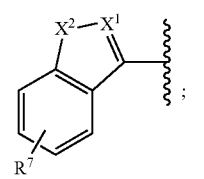

D and $R^2$, R', R", $R^3$, $R^4$, $R^5$, $R^6$, $R^7$, $X^1$, $X^{1'}$, $X^2$, and N are as defined in the specification. Compounds of the invention are useful for the treatment of neurological and neuropsychiatric disorders.

11 Claims, No Drawings

FOREIGN PATENT DOCUMENTS

| | | |
|---|---|---|
| WO | WO 99/44596 | 9/1999 |
| WO | WO 99/45011 | 9/1999 |
| WO | WO 01/81308 A2 | 11/2001 |
| WO | WO 02/22612 | 3/2002 |
| WO | WO 03/004480 | 1/2003 |
| WO | WO 03/010132 A1 | 2/2003 |
| WO | WO 03/035602 | 5/2003 |
| WO | WO 2004/037800 | 5/2004 |
| WO | WO 2004/072034 A1 | 8/2004 |
| WO | WO 2004/113280 A1 | 12/2004 |
| WO | WO 2005/023260 A1 | 3/2005 |
| WO | WO 2005/103042 A1 | 11/2005 |
| WO | WO 2005/110983 A1 | 11/2005 |

OTHER PUBLICATIONS

Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. in Neurobiol. vol. 67, pp. 173-202 (2002).
Carlsson M. L., J. Neural Trans. vol. 105, pp. 525-535 (1998).
Kwong et al., Org. Lett. 4, pp. 581-584 (2002).
Kuwano et al., JOC 67, pp. 6479-6486 (2002).
Chem. Abstract XP-002299148 Chemcats No. 2004:3653471 (2004).
Caulfield W. L. et al., Journal of Med. Chem. vol. 44(17) pp. 2679-2682 (2001).
Chem. Abstract XP-002299149 Chemcats No. 2004: 2179871 (2004).
Chemical Abstracts Service, Apr. 23, 2003, XP002308402, Database accession No. 2003: 2142911 Chemcats & Catalog: AsInExExpress Gold.
Chemical Abstracts Service, Jun. 6, 2003, XP002308481 & Database Chemcats.
Chemical Abstracts Service, Jan. 1, 2004, XP002308405, Database accession No. 2003:2872406 Chemcats & Catalog: Ambinter Stock Screening Collection.
Chemical Abstracts Service, Jan. 1, 2004, XP002308403, Database accession No. 2004:591813 & Catalog: Ambinter Stock Screening Collection.
Chemical Abstracts Service, Jan. 1, 2004, XP002308404, Database accession No. 2004:660630 & Catalog: Ambinter Screening Library.
Chemical Abstracts Service, XP002308978 Chemcats No. 2002:330684 (2003).
Chemical Abstracts Service, XP002308979; CHEMCATS No. 2003:1026314 (2004)
Chemical Abstracts Service, XP002308980; CHEMCATS No. 2001;2814605 (2003).
Chemical Abstracts Service, XP002308981; CHEMCATS No. 2002:2063001 (2004).
Chemical Abstracts Service, XP002308983; CHEMCATS No. 2003:1026533 (2004).
Chemical Abstracts Service, XP002308984; CHEMCATS No. 2002:2288893 (2004).
Chemical Abstracts Service, XP002308985; CHEMCATS No. 2003:709504 (2004).
Chemical Abstracts Service, XP002308986; CHEMCATS No. 2003:709503 (2004).
Chemical Abstracts Service, XP002308987; CHEMCATS No. 2003:709505 (2004).
Chemical Abstracts Service, XP002308988; CHEMCATS No. 2004:1498769 (2004).
Chemical Abstracts Service, XP002308989; CHEMCATS No. 2002:2386068 (2004).
Chemical Abstracts Service, XP002308990; CHEMCATS No. 2002:2894607 (2004).
Chemical Abstracts Service, XP002308991; CHEMCATS No. 2003:3342164 (2004).
Chemical Abstracts Service, XP002308992; CHEMCATS No. 2003:3345505 (2004).
Chemical Abstracts Service, XP002308993; CHEMCATS No. 2003:3346187 (2004).
Chemical Abstracts Service, XP002309007; CHEMCATS No. 2004:660630 (2004).
Abstract corresponding to Document B5—WO 03/035602 (2003).

PHENYL-PIPERAZINE METHANONE DERIVATIVES, SUBSTITUTED BY HETEROCYCLIC GROUPS

PRIORITY TO RELATED APPLICATIONS

This application claims the benefit of European Application No. 04106440.3, filed Dec. 9, 2004, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D. A. and Lieberman J. A., Neuron, 2000, 28:325-33). For decades research has focused on the "dopaminergic hyperactivity" hypothesis which has led to therapeutic interventions involving blockade of the dopaminergic system (Vandenberg R. J. and Aubrey K. R., Exp. Opin. Ther. Targets, 2001, 5(4): 507-518; Nakazato A and Okuyama S, et al., 2000, Exp. Opin. Ther. Patents, 10(1): 75-98). This pharmacological approach poorly address negative and cognitive symptoms which are the best predictors of functional outcome (Sharma T., Br. J. Psychiatry, 1999, 174(suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D. C. et al., 1999, Biol. Psychiatry, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A. R. et al., 1999, Cell, 98: 427-236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D. O., 1949, The organization of behavior, Wiley, NY; Bliss T. V. and Collingridge G. L., 1993, Nature, 361: 31-39). Transgenic mice overexpressing the NMDA NR2B subunit exhibit enhanced synaptic plasticity and superior ability in learning and memory (Tang J. P. et al., 1999, Nature: 401-63-69).

Thus, if a glutamate deficit is implicated in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R. R. et al, 2002, Trends in Pharm. Sci., 23(8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, Mol. Mem. Biol., 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, Proc. Natl. Acad. Sci. USA, 95: 15730-15734; Chen L. et al., 2003, J. Neurophysiol., 89 (2): 691-703).

Glycine transporters inhibitors are suitable for the treatment of neurological and neuropsychiatric disorders. The majority of diseases states implicated are psychoses, schizophrenia (Armer R. E. and Miller D. J., 2001, Exp. Opin. Ther. Patents, 11 (4): 563-572), psychotic mood disorders such as severe major depressive disorder, mood disorders associated with psychotic disorders such as acute mania or depression associated with bipolar disorders and mood disorders associated with schizophrenia, (Pralong E. T. et al., 2002, Prog. Neurobiol., 67: 173-202), autistic disorders (Carlsson M. L., 1998, J. Neural Transm. 105: 525-535), cognitive disorders such as dementias, including age related dementia and senile dementia of the Alzheimer type, memory disorders in a mammal, including a human, attention deficit disorders and pain (Armer R. E. and Miller D. J., 2001, Exp. Opin. Ther. Patents, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of the formula I

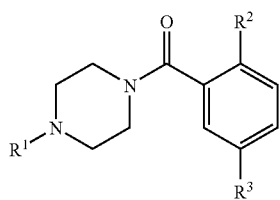

wherein

R[1] is the group

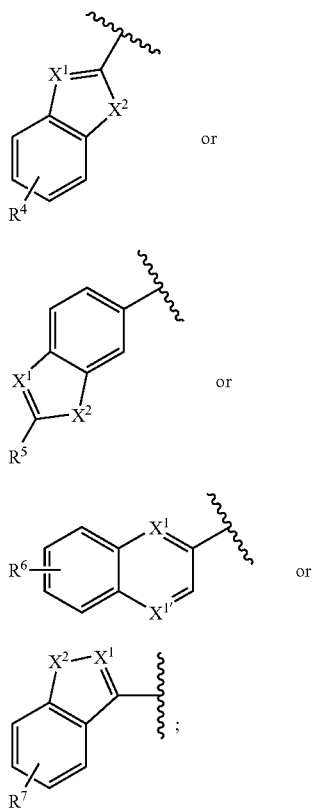

R[2] is a non aromatic heterocycle, OR' or N(R")$_2$;

R' is lower alkyl, lower alkyl substituted by halogen or —(CH$_2$)$_n$-cycloalkyl;

R" is lower alkyl;

R[3] is NO$_2$, CN or SO$_2$R';

R[4] is hydrogen, hydroxy, halogen, NO$_2$, lower alkyl, lower alkyl, substituted by halogen, lower alkoxy, SO$_2$R' or C(O)OR";

R[5], R[6], and R[7] are each independently hydrogen, halogen, lower alkyl or lower alkyl substituted by halogen;

X[1] and X[1'] are each independently CH or N, with the proviso that X[1] and X[1'] are not simultaneously CH;

X[2] is O, S, NH or N(lower alkyl); and n is 0, 1 or 2;

or to pharmaceutically active acid addition salt thereof.

The present invention also provides processes for preparing compounds of the invention and pharmaceutical compositions containing them. Furthermore, the invention includes all racemic mixtures, all their corresponding enantiomers and/or optical isomers. their use in the treatment of neurological and neuropsychiatric disorders.

Compounds of formula I are inhibitors of the glycine transporter 1 (GlyT-1), and have a good selectivity to glycine transporter 2 (GlyT-2) inhibitors. Therefore, the invention also provides methods for treating neurological and neuropsychiatric disorders, such as psychoses, disfunction in memory and learning. The invention further provides methods for the treatment of schizophrenia, dementia and other diseases in which cognitive processes are impaired, such as attention deficit disorders or Alzheimer's disease.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a saturated straight- or branched-chain group containing from 1 to 7 carbon atoms as defined above, which is attached via an oxygen atom.

As used herein, the term "cycloalkyl" denotes a saturated carbon ring, containing from 3 to 7 carbon atoms, for example, cyclopropyl, cyclopentyl or cyclohexyl.

As used herein the term "non aromatic heterocycle" denotes a five or six membered heterocyclic ring, containing one or two heteroatoms, selected from the group consisting of O, N or S. Examples of such rings are 1-pyrrolidine, 1-piperidine, 1-piperazine or 1-morpholine.

The term "halogen" denotes chlorine, iodine, fluorine and bromine.

As used herein the term "lower alkyl substituted by halogen" denotes an alkyl group as defined above, wherein at least one hydrogen atom is replaced by halogen, for example CF$_3$, CHF$_2$, CH$_2$F, CH$_2$CF$_3$ and the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present invention provides compounds of the formula I

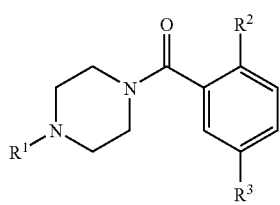

wherein

R¹ is the group

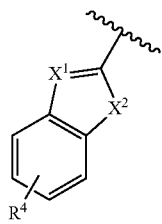  A or

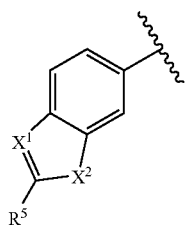  B or

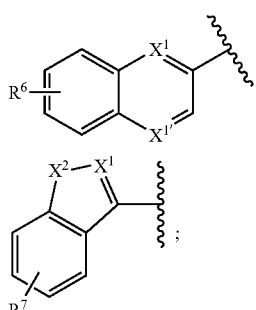  C or

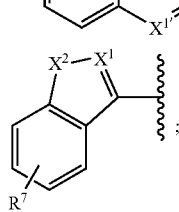  D

;

R² is a non aromatic heterocycle, OR' or N(R")₂;

R' is lower alkyl, lower alkyl substituted by halogen or —(CH₂)ₙ-cycloalkyl;

R" is lower alkyl;

R³ is NO₂, CN or SO₂R';

R⁴ is hydrogen, hydroxy, halogen, NO₂, lower alkyl, lower alkyl, substituted by halogen, lower alkoxy, SO₂R' or C(O) OR";

R⁵, R⁶, and R⁷ are each independently hydrogen, halogen, lower alkyl or lower alkyl substituted by halogen;

X¹ and X¹' are each independently CH or N, with the proviso that X¹ and X¹' are not simultaneously CH;

X² is O, S, NH or N(lower alkyl); and n is 0, 1 or 2;

or to pharmaceutically active acid addition salt thereof.

The following compounds of formulae IA, IB, IC and ID are encompassed by the present invention:

The invention provides compounds of formula IA

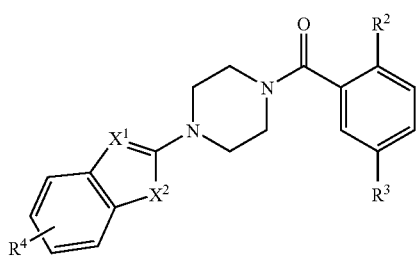

wherein

R² is a non aromatic heterocycle, OR' or N(R")₂;

R' is lower alkyl, lower alkyl, substituted by halogen or —(CH₂)ₙ-cycloalkyl;

R" is lower alkyl;

R³ is NO₂, CN or SO₂R';

R⁴ is hydrogen, hydroxy, halogen, NO₂, lower alkyl, lower alkyl, substituted by halogen, lower alkoxy, SO₂R' or C(O) OR";

X¹ is CH or N;

X² is O, S, NH or N(lower alkyl);

n is 0, 1 or 2;

or a pharmaceutically active acid addition salt thereof.

Preferred compounds of formula IA are the following:

[4-(6-chloro-benzothiazol-2-yl)-piperazin-1-yl]-(2-morpholin-4-yl-5-nitro-phenyl)-methanone,

[4-(6-chloro-benzothiazol-2-yl)-piperazin-1-yl]-(2-isopropoxy-5-methanesulfonyl-phenyl)-methanone, (4-benzooxazol-2-yl-piperazin-1-yl)-(2-cyclopentyloxy-5-methanesulfonyl-phenyl)-methanone, (4-benzooxazol-2-yl-piperazin-1-yl)-(2-isobutoxy-5-methanesulfonyl-phenyl)-methanone, (2-isopropoxy-5-methanesulfonyl-phenyl)-[4-(6-methoxy-benzothiazol-2-yl)-piperazin-1-yl]-methanone, (2-isopropoxy-5-methanesulfonyl-phenyl)-[4-(6-nitro-benzothiazol-2-yl)-piperazin-1-yl]-methanone, (2-isopropoxy-5-methanesulfonyl-phenyl)-[4-(4-methoxy-benzothiazol-2-yl)-piperazin-1-yl]-methanone, (2-isopropoxy-5-methanesulfonyl-phenyl)-[4-(4-nitro-benzothiazol-2-yl)-piperazin-1-yl]-methanone,

[4-(4-hydroxy-benzothiazol-2-yl)-piperazin-1-yl]-(2-isopropoxy-5-methanesulfonyl-phenyl)-methanone,

[4-(5-chloro-benzothiazol-2-yl)-piperazin-1-yl]-(2-isopropoxy-5-methanesulfonyl-phenyl)-methanone,

[4-(6-ethoxy-benzothiazol-2-yl)-piperazin-1-yl]-(2-isopropoxy-5-methanesulfonyl-phenyl)-methanone,

[4-(6-chloro-benzothiazol-2-yl)-piperazin-1-yl]-(2-cyclopropylmethoxy-5-methanesulfonyl-phenyl)-methanone and

[4-(6-chloro-benzothiazol-2-yl)-piperazin-1-yl]-[5-methanesulfonyl-2-((S)-2,2,2-trifluoro-1-methyl-ethoxy)-phenyl]-methanone.

The invention provides compound of formula

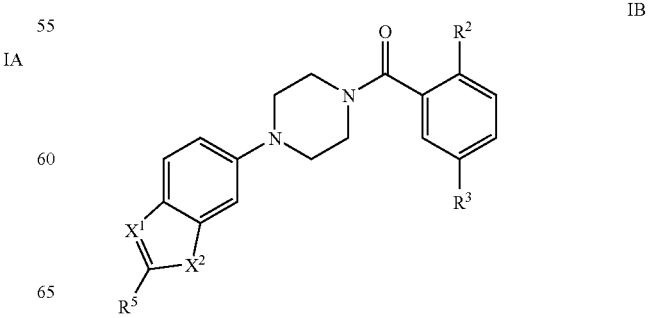

wherein

R² is a non aromatic heterocycle, OR' or N(R")₂;

R' is lower alkyl, lower alkyl, substituted by halogen or —(CH₂)ₙ-cycloalkyl;

R" is lower alkyl;

R³ is NO₂, CN or SO₂R';

R⁵ is hydrogen, halogen, lower alkyl or lower alkyl substituted by halogen;

X¹ is CH or N;

X² is O, S, NH or N(lower alkyl);

n is 0, 1 or 2;

or a pharmaceutically active acid addition salt thereof.

A preferred compound of formula IB is (2-isobutoxy-5-methanesulfonyl-phenyl)-[4-(2-methyl-benzothiazol-5-yl)-piperazin-1-yl]-methanone.

The invention provides compound of formula

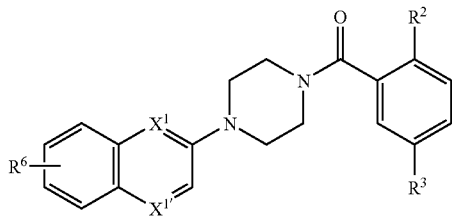

IC wherein

R² is a non aromatic heterocycle, OR' or N(R")₂;

R' is lower alkyl, lower alkyl substituted by halogen or —(CH₂)ₙ-cycloalkyl;

R" is lower alkyl;

R³ is NO₂, CN or SO₂R';

R⁶ is hydrogen, halogen, lower alkyl or lower alkyl substituted by halogen;

X¹ and X¹' are each independently CH or N, with the proviso that X¹ and X¹' are not simultaneously CH;

n is 0, 1 or 2;

or a pharmaceutically active acid addition salt thereof.

Preferred compounds of formula IC are (2-isobutoxy-5-methanesulfonyl-phenyl)-(4-quinolin-2-yl-piperazin-1-yl)-methanone,

[4-(6-chloro-quinolin-2-yl)-piperazin-1-yl]-(2-cyclopentyloxy-5-methanesulfonyl-phenyl)-methanone, (2-isobutoxy-5-methanesulfonyl-phenyl)-(4-quinoxalin-2-yl-piperazin-1-yl)-methanone, (2-isopropoxy-5-methanesulfonyl-phenyl)-(4-quinoxalin-2-yl-piperazin-1-yl)-methanone, (2-cyclopentyloxy-5-methanesulfonyl-phenyl)-(4-quinoxalin-2-yl-piperazin-1-yl)-methanone, (2-isobutoxy-5-methanesulfonyl-phenyl)-(4-quinolin-3-yl-piperazin-1-yl)-methanone and (2-cyclopentyloxy-5-methanesulfonyl-phenyl)-(4-quinolin-3-yl-piperazin-1-yl)-methanone.

The invention provides compound of formula

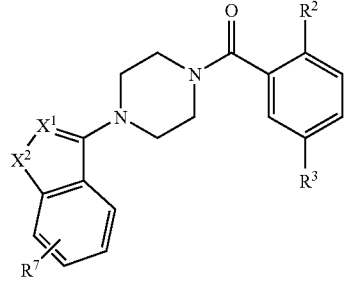

ID wherein

R² is a non aromatic heterocycle, OR' or N(R")₂;

R' is lower alkyl, lower alkyl substituted by halogen or —(CH₂)ₙ-cycloalkyl;

R" is lower alkyl;

R³ is NO₂, CN or SO₂R';

R⁷ is hydrogen, halogen, lower alkyl or lower alkyl substituted by halogen;

X¹ is CH or N;

X² is O, S, NH or N(lower alkyl);

n is 0, 1 or 2;

or a pharmaceutically active acid addition salt thereof.

Preferred compounds of formula ID are (4-benzo[d]isothiazol-3-yl-piperazin-1-yl)-(2-isopropoxy-5-methanesulfonyl-phenyl)-methanone, (4-benzo[d]isothiazol-3-yl-piperazin-1-yl)-(2-cyclopropylmethoxy-5-methanesulfonyl-phenyl)-methanone and (4-benzo[d]isothiazol-3-yl-piperazin-1-yl)-[5-methanesulfonyl-2-((S)-2,2,2-trifluoro-1-methylethoxy)-phenyl]-methanone.

Most preferred compounds of formula I are those of formulas IA and IC.

The present compounds of formula I and their pharmaceutically acceptable salts can be prepared by methods known in the art, for example, by processes described below, which process comprises a) reacting a compound of formula

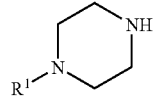

II with a compound of formula

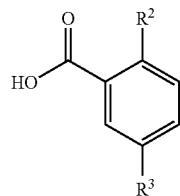

III in the presence of an activating agent, such as TBTU, to produce a compound of formula

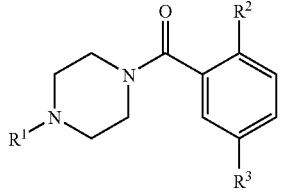

wherein the substituents are as defined above, or b) reacting a compound of formula

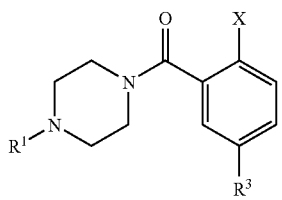

with a compound of formula

R²H    V in the presence of a base like potassium carbonate, or with addition of a catalyst like Cu(I)I to produce a compound of formula

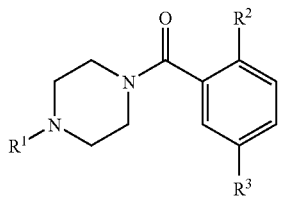

wherein the substituents $R^1$, $R^2$ and $R^3$ are as defined above, and X is halogen, or c) reacting a compound of formula

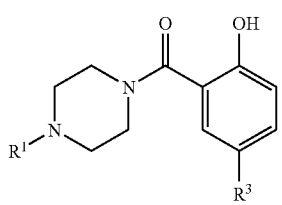

with a compound of formula

R'X    VI to produce a compound of formula

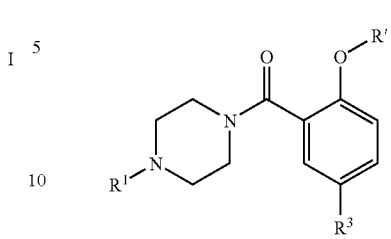

wherein the substituents $R^1$ and $R^3$ are as defined above, and R' is lower alkyl, lower alkyl, substituted by halogen or —(CH₂)$_n$-cycloalkyl and X is halogen;

or d) reacting a compound of formula

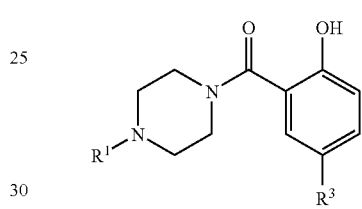

with a compound of formula

R'OH    VII under Mitsunobu conditions to produce a compound of formula

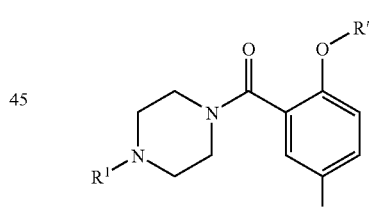

wherein the substituents $R^1$ and $R^3$ are as defined above, and R' is lower alkyl, lower alkyl, substituted by halogen or —(CH₂)$_n$-cycloalkyl, and if desired, converting the compounds obtained into pharmaceutically acceptable acid addition salts.

The compounds of formula I can be prepared in accordance with process variants a), b) c) or d) and with the following schemes 1, 2, 3 and 4. All starting materials are either commercially available, described in the literature or can be prepared by methods well known in the art.

The following abbreviation has been used:

TBTU=(2-(1H-benzotriazole-1-yl)-1,1,3,3-tetramethyluroniumtetrafluoroborate)

Scheme 1

Preparation of compounds of formulas II and I

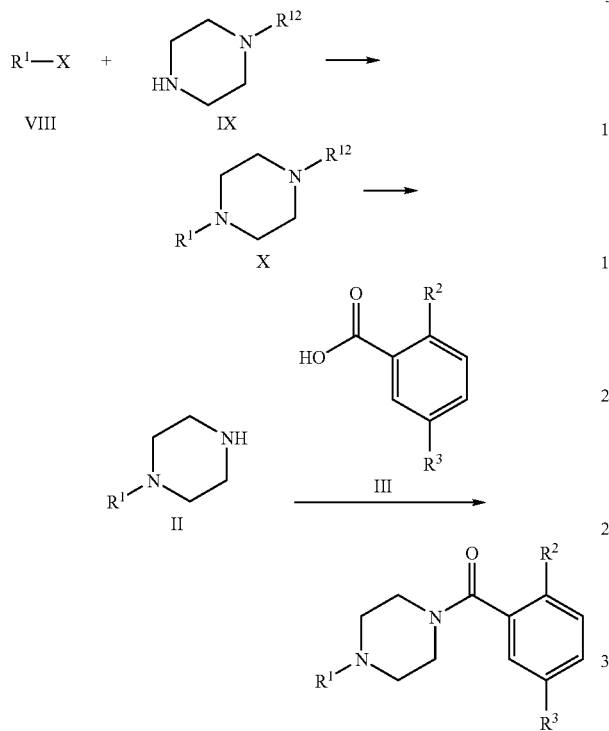

wherein $R^1$, $R^2$ and $R^3$ are as described above, $R^{12}$ is hydrogen or a protecting group, such as tert-butyloxycarbonyl or benzyloxycarbonyl, and X is halogen, mesylate or triflate.

When X is an activated leaving group (for examples in o-position to a nitrogen atom), the compounds of formula X are obtained by heating a compound of formula VIII in the presence of a compound of formula IX and a base like potassium- or sodium carbonate in a suitable solvent like alcohol, acetone or acetonitrile.

When X is an unactivated leaving group, compounds X are obtained by known Pd- or Cu-catalyzed coupling reactions between compounds of formulas VIII and IX (see for example S. L. Buchwald ea., Org. Lett. 4, 581 (2002) or J. F. Hartwig ea., JOC 67, 6479 (2002)). When $R^{12}$ is a protective group, deprotection by methods known in the art yields compounds of formula II. A compound of formula II is then treated with a compound of formula III in the presence of TBTU and a base, such as N-ethyldiisopropylamine to obtain a compound of formula I.

Scheme 2

Preparation of compounds of formula III:

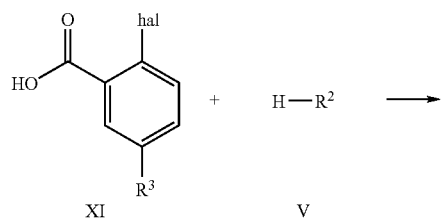

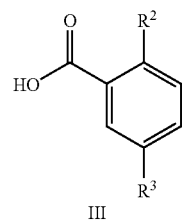

wherein $R^2$ and $R^3$ are as described above and hal is halogen.

Compounds of formula III can be prepared in conventional manner. If H—$R^2$ is a non aromatic heterocycle, for example morpholine, the reaction is carried out at room temperature for about 2 hours.

If $R^2$ is OR' for R' is lower alkyl, lower alkyl substituted by halogen or —$(CH_2)_n$-cycloalkyl, the reaction is carried out with the corresponding alcohol of formula V by reaction with a mixture of a compound of formula XI and Cu(I)Br in triethylamine.

Scheme 3

Preparation of compounds of formula I:

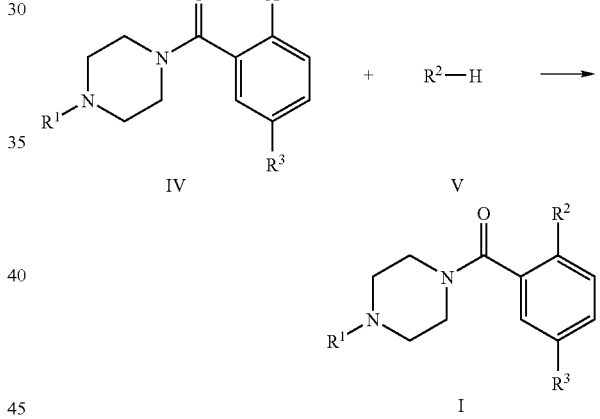

wherein $R^1$, $R^2$ and $R^3$ are as described above and X is halogen.

X can be replaced by $R^2$ in conventional manner, in presence of a base such as triethylamine or with addition of a catalyst like Cu(I)Br.

Scheme 4

Preparation of compounds of formula I2:

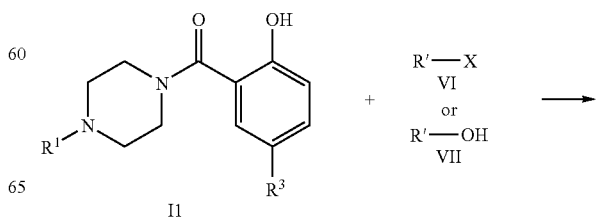

-continued

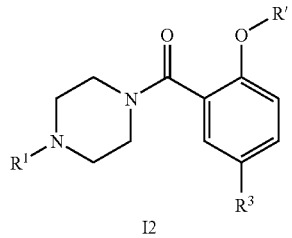

wherein R', R¹ and R³ are as described above and X is halogen.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin1% (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [³H]-glycine 60 nM (11-16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

Representative compounds show an $IC_{50}$ (µM) at GlyT-1<0.5.

| Example No. | $IC_{50}$ (µM) |
|---|---|
| 1.1 formula IA | 0.271 |
| 1.2 formula IA | 0.398 |
| 1.4 formula IA | 0.097 |
| 1.5 formula IA | 0.144 |
| 1.8 formula IA | 0.174 |
| 1.9 formula IA | 0.206 |
| 1.11 formula IA | 0.148 |
| 1.12 formula IA | 0.375 |
| 1.13 formula IA | 0.158 |
| 1.14 formula IA | 0.218 |
| 1.19 formula IC | 0.078 |
| 1.22 formula IC | 0.399 |
| 1.15 formula IA | 0.339 |
| 1.17 formula IB | 0.440 |
| 1.23 formula IC | 0.167 |
| 1.24 formula IC | 0.287 |
| 1.25 formula IC | 0.067 |
| 1.27 formula IC | 0.082 |
| 1.28 formula IC | 0.149 |
| 1.29 formula ID | 0.500 |
| 1.31 formula ID | 0.467 |
| 1.33 formula ID | 0.055 |
| 1.39 formula IA | 0.230 |
| 1.40 formula IA | 0.039 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of the invention, but as a rule are not necessary. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injection solutions.

Compounds of the invention are GlyT-1 inhibitors and have good selectivity to GlyT-2 inhibitors. Thus, the compounds are useful for the treatment of diseases related to activation of NMDA receptors via GlyT-1 inhibition. The most preferred indications in accordance with the present invention are those, which include disorders of the central nervous system. For example, the present invention provides a method for treating schizophrenia which comprises administering to an individual a therapeutically effective amount of a compound of formula I or a pharmaceutically acceptable salt thereof. The present invention also provides a method for treating cognitive impairment which comprises administering to an individual a therapeutically effective amount of a compound of formula I or a pharmaceutically acceptable salt thereof. The present invention further provides a method for treating Alzheimer's disease which comprises administering to an individual a therapeutically effective amount of a compound of formula I or a pharmaceutically acceptable salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula IA or IB | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula IA or IB | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following examples illustrate the present invention without limiting it. All temperatures are given in degree Celsius.

All starting materials are either commercially available, described in the literature (CA-abstract-numbers are given) or or can be prepared by methods well known in the art.

EXAMPLE 1.1

Preparation of [4-(6-Chloro-benzothiazol-2-yl)-piperazin-1-yl]-(2-morpholin-4-yl-5-nitro-phenyl)-methanone (a) 6-Chloro-2-piperazin-1-yl-benzothiazole

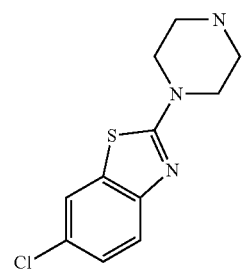

A mixture of 10 mmol 2,6-dichlorobenzothiazole, 12.3 mmol of piperazine and 20 mmol of potassium carbonate in 50 ml of acetonitrile was refluxed for 3 hours. The reaction mixture was concentrated and treated with 25 ml of water. Extraction with ethyl acetate, drying over magnesium sulfate, and evaporation of the solvent yielded the title compound as a colorless solid.

MS (m/e): 254.7 (MH$^+$)

(b) [4-(6-Chloro-benzothiazol-2-yl)-piperazin-1-yl]-(2-morpholin-4-yl-5-nitro-phenyl)-methanone

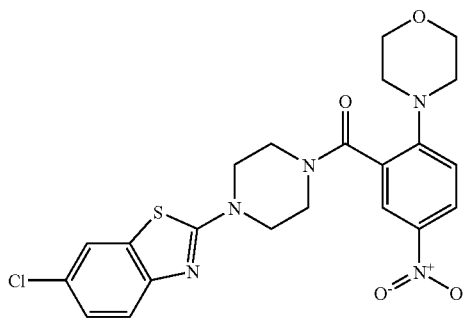

To a solution of 0.25 mmol 2-morpholin-4-yl-5-nitro-benzoic acid (Example 2.1) in 0.7 ml dimethylformamide 0.26 mmol TBTU, 1.6 mmol N-ethyldiisopropylamine and 0.25 mmol 6-chloro-2-piperazin-1-yl-benzothiazole were successively added. The reaction was then stirred at RT for two hours, concentrated in vacuo and treated with 5 ml water. The solid is filtered off and recrystallized form methanol to yield the title compound as a yellow solid.

MS (m/e): 488.1 (M+H$^+$)

EXAMPLE 1.2

Preparation of [4-(6-Chloro-benzothiazol-2-yl)-piperazin-1-yl]-(2-isopropoxy-5-methanesulfonyl-phenyl)-methanone

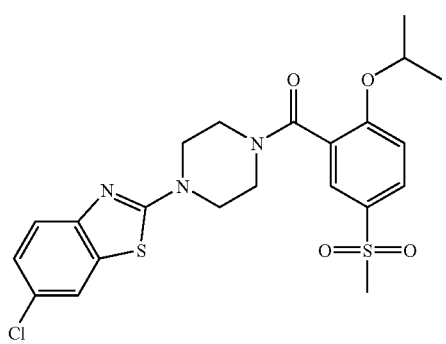

Prepared in analogy to example 1.1 b) from 2-isopropoxy-5-methanesulfonyl-benzoic acid (Example 2.2) and 6-chloro-2-piperazin-1-yl-benzothiazole. The crude material was purified by chromatography (SiO$_2$, CH$_2$Cl$_2$/MeOH=95/5) to yield the title compound as a yellowish solid. MS (m/e): 552.3 (M+CH$_3$COOH$^+$)

EXAMPLE 1.3

Preparation of (4-Benzoxazol-2-yl-piperazin-1-yl)-(2-isopropoxy-5-methanesulfonyl-phenyl)-methanone (a) 4-Benzoxazol-2-yl-piperazine-1-carboxylic acid tert.-butyl ester

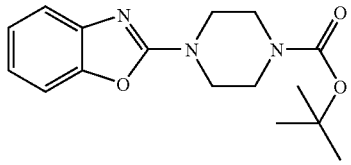

A mixture of 52.5 mmol 2-chlorobenzoxazol, 53.6 mmol piperazine-1-carboxylic acid tert-butyl ester and 63 mmol of potassium carbonate in 60 ml of acetonitrile was refluxed for 16 hours. The reaction mixture was conentrated, diluted with water and extracted with ethyl acetate. The organic phase was dried and concentrated to yield the title compounds as a slightly orange solid. MS (m/e): 304.2 (M+H$^+$)

(b) 2-piperazin-1-yl-benzoxazole hydrochloride

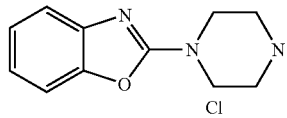

10.8 mmol of 4-benzoxazol-2-yl-piperazine-1-carboxylic acid tert.-butyl ester were treated with 30 ml of a dioxane, saturated with gaseous hydrochloric acid. The heterogenous mixture was stirred at room temperature for 1 hour, before evaporation of the solvent. This yielded the title compound as a colorless solid.

MS (m/e): 204.1 (M+H$^+$)

(c) 4-Benzoxazol-2-yl-piperazin-1-yl)-(2-isopropoxy-5-methanesulfonyl-phenyl)-methanone

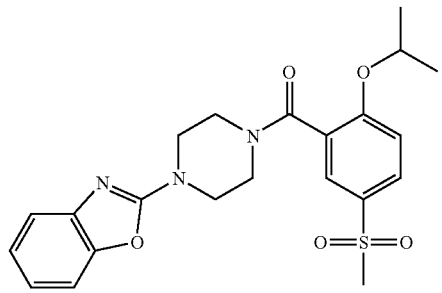

Prepared in analogy to example 1.1 b) from 2-isopropoxy-5-methanesulfonyl-benzoic acid (Example 2.2) and 2-piperazin-1-yl-benzoxazole hydrochloride. The crude material was triturated with diethyl ether to yield the title compound as a colorless solid.

MS (m/e): 444.1 (M+H$^+$)

EXAMPLE 1.4

Preparation of (4-Benzoxazol-2-yl-piperazin-1-yl)-(2-cyclopentyloxy-5-methanesulfonyl-phenyl)-methanone

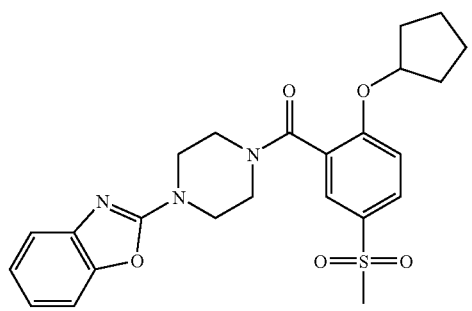

Prepared in analogy to example 1.1 b) from 2-cyclopentyloxy-5-methanesulfonyl-benzoic acid (Example 2.3) and 2-piperazin-1-yl-benzoxazole hydrochloride. The crude material was purified by chromatography (SiO$_2$, ethyl acetate) to yield the title compound as a colorless solid.

MS (m/e): 470.1 (M+H$^+$)

EXAMPLE 1.5

Preparation of (4-Benzoxazol-2-yl-piperazin-1-yl)-(2-isobutoxy-5-methanesulfonyl-phenyl)-methanone

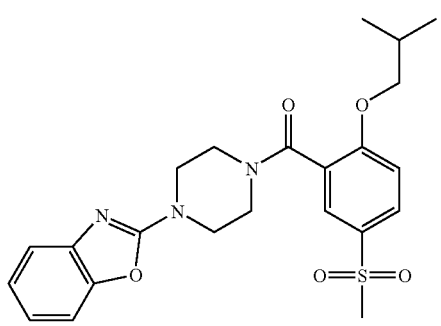

Prepared in analogy to example 1.1 b) from 2-isobutoxy-5-methanesulfonyl-benzoic acid (Example 2.4) and 2-piperazin-1-yl-benzoxazole hydrochloride. The crude material was purified by chromatography (SiO$_2$, ethyl acetate) to yield the title compound as a slightly yellow solid.

MS (m/e): 458.1 (M+H$^+$)

EXAMPLE 1.6

Preparation of (2-Cyclopentyloxy-5-methanesulfonyl-phenyl)-[4-(5-ethanesulfonyl-benzoxazol-2-yl)-piperazin-1-yl]-methanone (a) 5-Ethanesulfonyl-benzoxazole-2-thiol

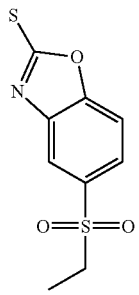

100 mmol 1-amino-5-ethylsulfonyl-2-hydroxybenzene were dissolved in 200 ml of ethanol and 150 ml of carbon disulfide. 120 mmol of potassium hydroxide was added and the mixture refluxed over night. The solvent was evaporated, the residue treated with 1 M hydrochloric acid, extracted with ethyl acetate and dried. Evaporation gave the crude product which was recrystallized from ethyl acetate to yield the title compound as yellowish solid.

MS (m/e): 242.4 (M−H)

(b) 2-Chloro-5-ethanesulfonyl-benzoxazole

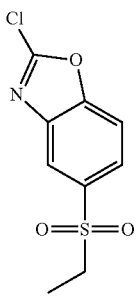

8 mmol of 5-Ethanesulfonyl-benzooxazole-2-thiol were dissolved in 10 ml of thionyl chloride. 1 drop of N,N-dimethylformamide is added and the reaction mixture hold at 65° for 45 min. Evaporation of the solvent yields the title compound as brownish solid.

MS (m/e): 262.9 (M+NH$_4^+$)

(c) 4-(5-Ethanesulfonyl-benzoxazol-2-yl)-piperazine-1-carboxylic acid tert.-butyl ester

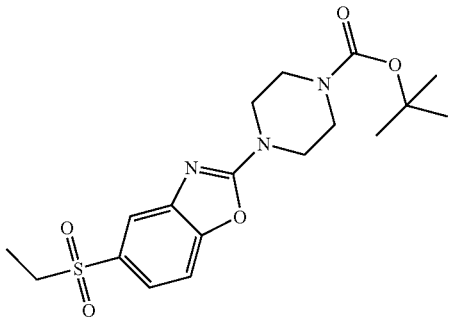

A mixture of 8.1 mmol of 2-chloro-5-ethanesulfonyl-benzoxazole, 8.3 mmol piperazine-1-carboxylic acid tert-butyl ester and 9.8 mmol of potassium carbonate in 20 ml of acetonitrile was refluxed for 16 hours. The reaction mixture was cooled, concentrated in vacuo and treated with 50 ml water. Extraction with ethyl acetate and recrystallisation from a concentrated ethyl acetate solution yielded the title compound as a brownish solid.

MS (m/e): 454.4 (M+CH$_3$COO)

(d) 5-Ethanesulfonyl-2-piperazin-1-yl-benzoxazole hydrochloride

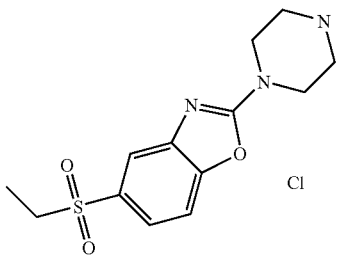

10.8 mmol of -(5-Ethanesulfonyl-benzoxazol-2-yl)-piperazine-1-carboxylic acid tert.-butyl ester were treated with 256 ml of a dioxane, saturated with gaseous hydrochloric acid. The heterogenous mixture was stirred overnight at room temperature. Evaporation of the solvent yielded the title compound as a colorless solid.

MS (m/e): 296.4 (M+H⁺)

(e) (2-Cyclopentyloxy-5-methanesulfonyl-phenyl)-[4-(5-ethanesulfonyl-benzoxazol-2-yl)-piperazin-1-yl]-methanone

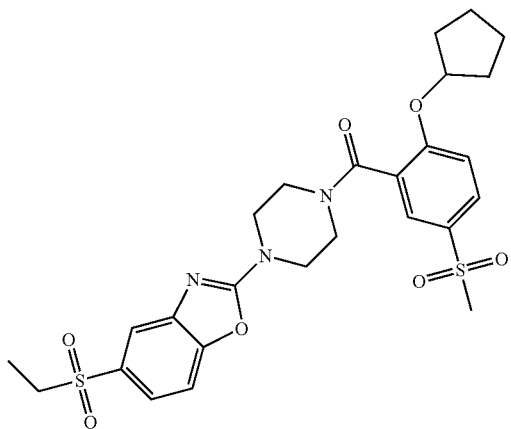

Prepared in analogy to example 1.1 b) from 2-cyclopentyloxy-5-methanesulfonyl-benzoic acid (Example 2.3) and 5-ethanesulfonyl-2-piperazin-1-yl-benzoxazole hydrochloride. The crude material was purified by chromatography (SiO₂, ethyl acetate) to yield the title compound as a colorless solid.

MS (m/e): 562.3 (M+H⁺)

EXAMPLE 1.7

Preparation of [4-(5-Ethanesulfonyl-benzoxazol-2-yl)-piperazin-1-yl]-(2-isobutoxy-5-methanesulfonyl-phenyl)-methanone

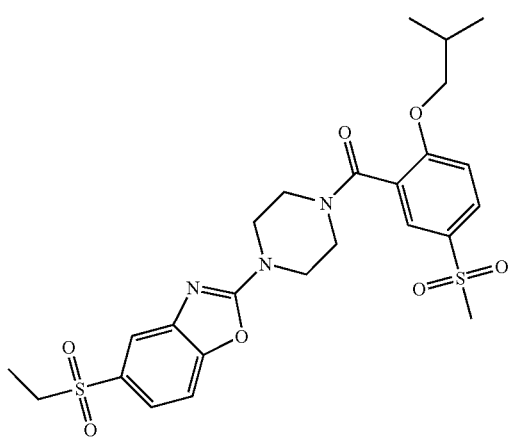

Prepared in analogy to example 1.1 b) from 2-isobutoxy-5-methanesulfonyl-benzoic acid (Example 2.4) and 5-ethanesulfonyl-2-piperazin-1-yl-benzoxazole hydrochloride. The crude material was purified by chromatography (SiO₂, ethyl acetate) to yield the title compound as a colorless solid.

MS (m/e): 550.2 (M+H⁺)

EXAMPLE 1.8

Preparation of (2-Isopropoxy-5-methanesulfonyl-phenyl)-[4-(6-methoxy-benzothiazol-2-yl)-piperazin-1-yl]-methanone (a) 6-Methoxy-2-piperazin-1-yl-benzothiazole

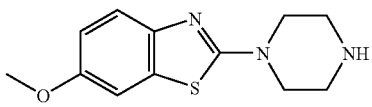

A mixture of 1.50 mmol 2-chloro-6-methoxybenzothiazole (CA=[2605-14-3]), 4.51 mmol of piperazine and 4.51 mmol of triethylamine in 5 ml of tetrahydrofuran in a sealed tube was heated at 160° C. for 5 min under microwave irradiation. The reaction mixture was concentrated, and the residue was purified by chromatography (SiO₂, methanol/dichloromethane) to yield the title compound as a white solid.

MS (m/e): 250.3 (M+H⁺)

(b) (2-Isopropoxy-5-methanesulfonyl-phenyl)-[4-(6-methoxy-benzothiazol-2-yl)-piperazin-1-yl]-methanone

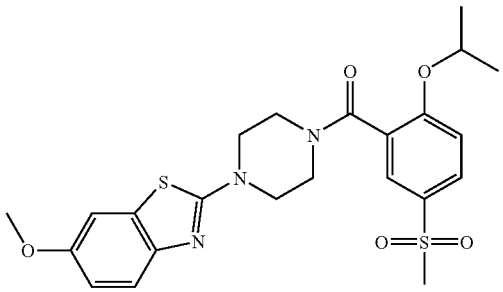

Prepared in analogy to example 1.1 b) from 2-Isopropoxy-5-methanesulfonyl-benzoic acid (Example 2.2) and 6-Methoxy-2-piperazin-1-yl-benzothiazole in tetrahydrofuran. The crude material was purified by chromatography (SiO₂, heptane/ethyl acetate) to yield the title compound as a white foam.

MS (m/e): 490.3 (M+H⁺)

EXAMPLE 1.9

Preparation of (2-Isopropoxy-5-methanesulfonyl-phenyl)-[4-(6-nitro-benzothiazol-2-yl)-piperazin-1-yl]-methanone (a) 6-Nitro-2-piperazin-1-yl-benzothiazole

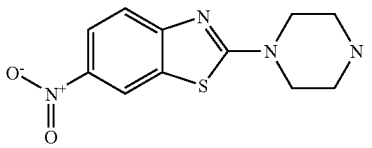

A mixture of 1.40 mmol 2-chloro-6-nitrobenzothiazole (CA=[2407-11-6]), 4.19 mmol of piperazine and 4.19 mmol of triethylamine in 5 ml of tetrahydrofuran in a sealed tube was heated at 160° C. for 10 min under microwave irradiation. The reaction mixture was concentrated, and the residue was purified by chromatography (SiO$_2$, methanol/dichloromethane) to yield the title compound as a yellow solid.

MS (m/e): 264.9 (M+H$^+$)

(b) (2-Isopropoxy-5-methanesulfonyl-phenyl)-[4-(6-nitro-benzothiazol-2-yl)-piperazin-1-yl]-methanone

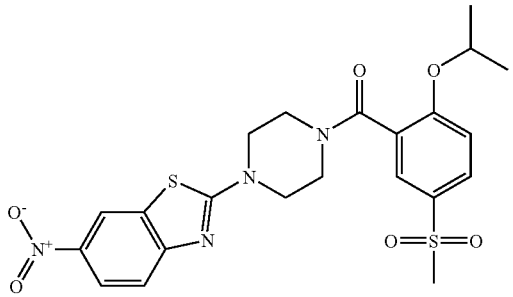

Prepared in analogy to example 1.1 b) from 2-Isopropoxy-5-methanesulfonyl-benzoic acid (Example 2.2) and 6-Nitro-2-piperazin-1-yl-benzothiazole in tetrahydrofuran. The crude material was purified by chromatography (SiO$_2$, heptane/ethyl acetate), and the residue was then triturated in ether to yield the title compound as a yellow solid.

MS (m/e): 505.3 (M+H$^+$)

EXAMPLE 1.10

Preparation of (2-[4-(2-Isopropoxy-5-methanesulfonyl-benzoyl)-piperazin-1-yl]-benzothiazole-4-carboxylic acid methyl ester

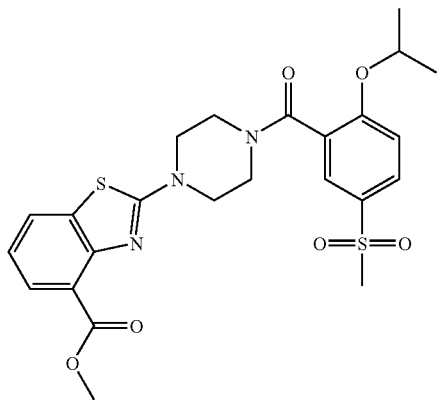

Prepared in analogy to example 1.1 b) from 2-isopropoxy-5-methanesulfonyl-benzoic acid (Example 2.2) and 2-Piperazin-1-yl-benzothiazole-4-carboxylic acid methyl ester hydrochloride in tetrahydrofuran. The crude material was purified by chromatography (SiO$_2$, heptane/ethyl acetate), and the residue was then triturated in ether to yield the title compound as a white solid.

MS (m/e): 518.5 (M+H$^+$)

EXAMPLE 1.11

Preparation of (2-Isopropoxy-5-methanesulfonyl-phenyl)-[4-(4-methoxy-benzothiazol-2-yl)-piperazin-1-yl]-methanone

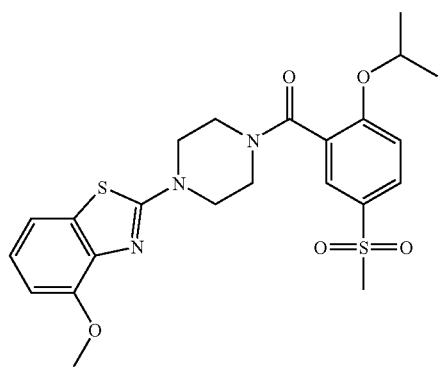

Prepared in analogy to example 1.1 b) from 2-isopropoxy-5-methanesulfonyl-benzoic acid (Example 2.2) and 4-Methoxy-2-piperazin-1-yl-benzothiazole hydrochloride in tetrahydrofuran. The crude material was purified by chromatography (SiO$_2$, heptane/ethyl acetate), and the residue was then triturated in ether to yield the title compound as a white solid.

MS (m/e): 490.5 (M+H$^+$)

EXAMPLE 1.12

Preparation of (2-Isopropoxy-5-methanesulfonyl-phenyl)-[4-(4-nitro-benzothiazol-2-yl)-piperazin-1-yl]-methanone

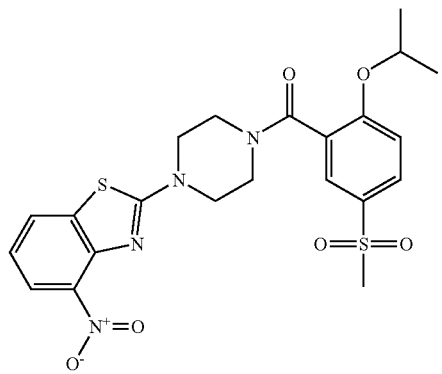

Prepared in analogy to example 1.1 b) from 2-isopropoxy-5-methanesulfonyl-benzoic acid (Example 2.2) and 4-Nitro-2-piperazin-1-yl-benzothiazole hydrochloride in tetrahydrofuran. The crude material was purified by chromatography (SiO$_2$, heptane/ethyl acetate), and the residue was then triturated in ether to yield the title compound as a white solid.

MS (m/e): 505.3 (M+H$^+$)

EXAMPLE 1.13

Preparation of [4-(4-Hydroxy-benzothiazol-2-yl)-piperazin-1-yl]-(2-isopropoxy-5-methanesulfonyl-phenyl)-methanone

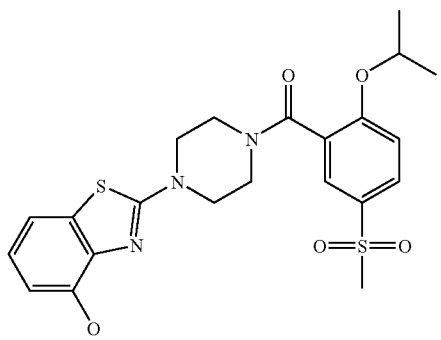

Prepared in analogy to example 1.1 b) from 2-isopropoxy-5-methanesulfonyl-benzoic acid (Example 2.2) and 2-Piperazin-1-yl-benzothiazol-4-ol hydrochloride in tetrahydrofuran. The crude material was purified by chromatography (SiO$_2$, heptane/ethyl acetate), and the residue was then triturated in ether to yield the title compound as a white solid.

MS (m/e): 476.0 (M+H$^+$)

EXAMPLE 1.14

Preparation of [4-(5-Chloro-benzothiazol-2-yl)-piperazin-1-yl]-(2-isopropoxy-5-methanesulfonyl-phenyl)-methanone (a) 5-Chloro-2-piperazin-1-yl-benzothiazole

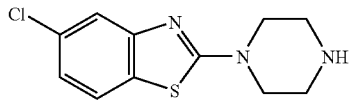

A mixture of 0.49 mmol 2,5-dichlorobenzothiazole (CA=[2941-48-2]), 1.47 mmol of piperazine and 1.47 mmol of triethylamine in 5 ml of tetrahydrofuran in a sealed tube was heated at 160° C. for 5 min under microwave irradiation. The reaction mixture was concentrated, and the residue was purified by chromatography (SiO$_2$, methanol/dichloromethane) to yield the title compound as a white solid.

MS (m/e): 254.1 ({$^{35}$Cl}M+H$^+$), 256.2 ({$^{37}$Cl}M+H$^+$)

(b) [4-(5-Chloro-benzothiazol-2-yl)-piperazin-1-yl]-(2-isopropoxy-5-methanesulfonyl-phenyl)-methanone

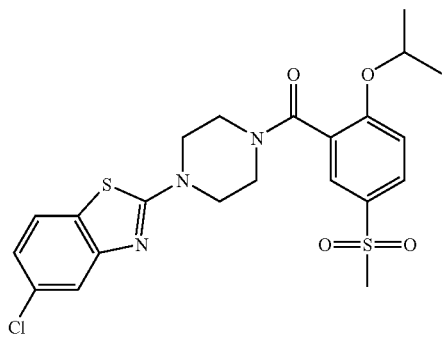

Prepared in analogy to example 1.1 b) from 2-isopropoxy-5-methanesulfonyl-benzoic acid (Example 2.2) and 5-chloro-2-piperazin-1-yl-benzothiazole in tetrahydrofuran. The crude material was purified by chromatography (SiO$_2$, heptane/ethyl acetate), and the residue was then triturated in ether to yield the title compound as a white solid.

MS MS (m/e): 494.3 ({$^{35}$Cl}M+H$^+$), 496.2 ({$^{37}$Cl}M+H$^+$)

EXAMPLE 1.15

Preparation of [4-(6-Ethoxy-benzothiazol-2-yl)-piperazin-1-yl]-(2-isopropoxy-5-methanesulfonyl-phenyl)-methanone (a) 6-Ethoxy-2-piperazin-1-yl-benzothiazole

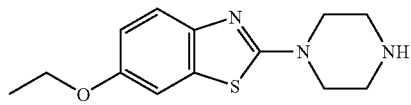

A mixture of 1.36 mmol 2-chloro-6-ethoxy-benzothiazole (CA=[79071-17-3]), 3.00 mmol of piperazine and 3.00 mmol of triethylamine in 5 ml of tetrahydrofuran in a sealed tube was heated at 160° C. for 5 min under microwave irradiation. The reaction mixture was concentrated, and the residue was purified by chromatography (SiO$_2$, methanol/dichloromethane) to yield the title compound as a white solid.

MS (m/e): 264.3 (M+H$^+$)

(b) [4-(6-Ethoxy-benzothiazol-2-yl)-piperazin-1-yl]-(2-isopropoxy-5-methanesulfonyl-phenyl)-methanone

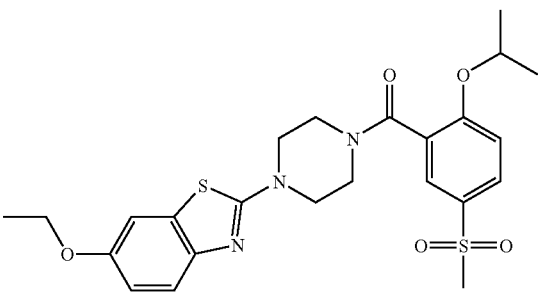

Prepared in analogy to example 1.1 b) from 2-isopropoxy-5-methanesulfonyl-benzoic acid (Example 2.2) and 6-ethoxy-2-piperazin-1-yl-benzothiazole in tetrahydrofuran. The crude material was purified by chromatography (SiO$_2$, heptane/ethyl acetate), and the residue was then triturated in ether to yield the title compound as a white solid.

MS MS (m/e): 504.1 (M+H$^+$)

EXAMPLE 1.16

Preparation of (2-Isopropoxy-5-methanesulfonyl-phenyl)-[4-(2-methyl-benzothiazol-5-yl)-piperazin-1-yl]-methanone (a) 4-(2-Methyl-benzothiazol-5-yl)-piperazine-1-carboxylic acid tert.-butyl ester

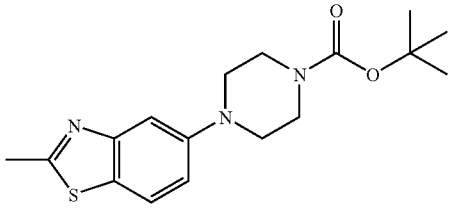

To a mixture of 1.3 mmol 5-bromo-2-methylbenzothiazole, 1.4 mmol piperazine-1-carboxylic acid, 2.0 mmol potassium hydroxide, 0.01 mmol bis(tri-tert.butylphosphine)palladium and 0.01 mmol cetyltrimethylammonium bromide in 1 ml toluene 1 drop of water is added. The reaction mixture is heated overnight under argon at 90° C. Addition of water and extraction with ethyl acetate gives a brownish oil which is purified by chromatography (SiO₂; cyclohexane/ethyl acetate 7:3) to yield the title compound as a yellowish solid.

MS (m/e): 334.4 (M+H⁺)

(b) 2-Methyl-5-piperazin-1-yl-benzothiazole hydrochloride

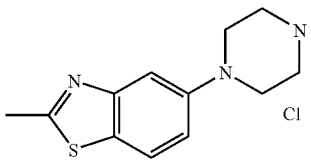

Prepared in analogy to example 1.6 (d) from 4-(2-methyl-benzothiazol-5-yl)-piperazine-1-carboxylic acid tert.-butyl ester and dioxane saturated with gaseous hydrochloric acid.

MS (m/e): 234.1 (M+H⁺)

(c) (2-Isopropoxy-5-methanesulfonyl-phenyl)-[4-(2-methyl-benzothiazol-5-yl)-piperazin-1-yl]-methanone

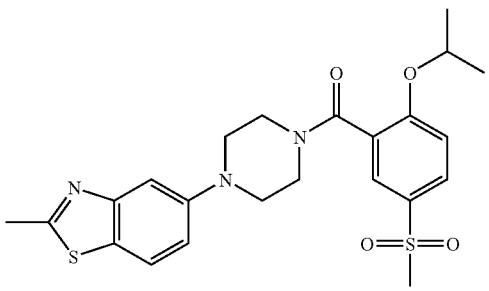

Prepared in analogy to example 1.1 (b) from 2-methyl-5-piperazin-1-yl-benzothiazole hydrochloride and 2-isopropoxy-5-methanesulfonyl-benzoic acid (example 2.2) in acetonitrile. Trituration in diethyl ether yields the title compound as a yellowish solid.

MS (m/e): 474.1 (M+H⁺)

EXAMPLE 1.17

Preparation of (2-Isobutoxy-5-methanesulfonyl-phenyl)-[4-(2-methyl-benzothiazol-5-yl)-piperazin-1-yl]-methanone

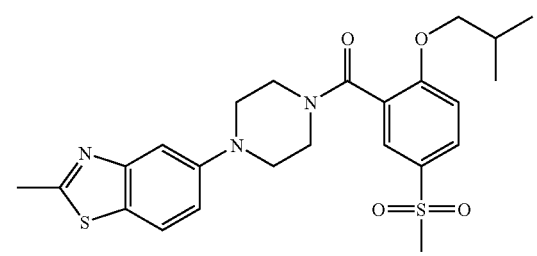

Prepared in analogy to example 1.1 (b) from 2-methyl-5-piperazin-1-yl-benzothiazole hydrochloride and 2-isobutoxy-5-methanesulfonyl-benzoic acid (example 2.4) in acetonitrile. Chromatography (SiO2; ethyl acetate) yields the title compound as a brownish solid.

MS (m/e): 488.4 (M+H⁺)

EXAMPLE 1.18

Preparation of (2-Isopropoxy-5-methanesulfonyl-phenyl)-(4-quinolin-2-yl-piperazin-1-yl)-methanone (a) 4-Quinolin-2-yl-piperazine-1-carboxylic acid tert.-butyl ester

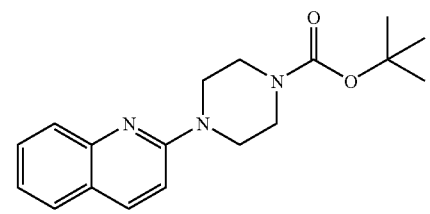

A mixture of 6.1 mmol 2-chloroquinoline, 6.7 mmol piperazine-1-carboxylic acid tert-butyl ester and 12.2 mmol potassium carbonate in 15 ml acetonitrile was refluxed overnight. The reaction mixture is concentrated, water is added and the compound extracted with ethyl acetate. Chromatography (SiO₂; cyclohexane/ethyl acetate 9/1) gave the title compound as a colorless solid.

MS (m/e): 314.3 (M+H⁺)

(b) 2-Piperazin-1-yl-quinoline hydrochloride

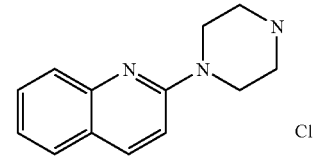

Prepared in analogy to example 1.6 (d) from 4-quinolin-2-yl-piperazine-1-carboxylic acid tert.-butyl ester and dioxane saturated with gaseous hydrochloric acid.

MS (m/e): 214.4 (M+H⁺)

(c) (2-Isopropoxy-5-methanesulfonyl-phenyl)-(4-quinolin-2-yl-piperazin-1-yl)-methanone

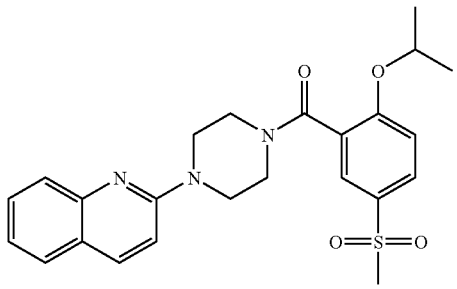

Prepared in analogy to example 1.1 (b) from 2-piperazin-1-yl-quinoline hydrochloride and 2-isopropoxy-5-methanesulfonyl-benzoic acid (example 2.2) in acetonitrile. Trituration in diethyl ether yields the title compound as a yellowish foam.
MS (m/e): 454.4 (M+H$^+$)

EXAMPLE 1.19

Preparation of (2-Isobutoxy-5-methanesulfonyl-phenyl)-(4-quinolin-2-yl-piperazin-1-yl)-methanone

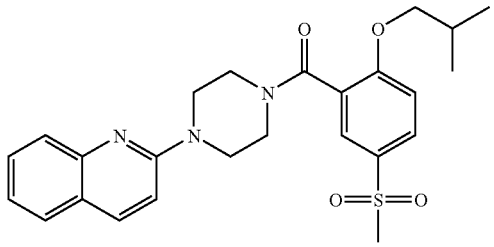

Prepared in analogy to example 1.1 (b) from 2-piperazin-1-yl-quinoline hydrochloride and 2-isobutoxy-5-methanesulfonyl-benzoic acid (example 2.4) in acetonitrile. Chromatography (SiO$_2$; ethyl acetate) yields the title compound as a yellowish solid.
MS (m/e): 468.4 (M+H$^+$)

EXAMPLE 1.20

Preparation of [4-(6-Chloro-quinolin-2-yl)-piperazin-1-yl]-(2-isopropoxy-5-methanesulfonyl-phenyl)-methanone (a) 4-(6-Chloro-quinolin-2-yl)-piperazine-1-carboxylic acid tert.-butyl ester

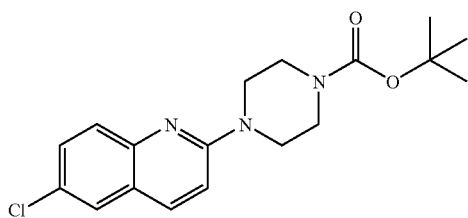

Prepared in analogy to example 1.18 (a) from 2,6-dichloroquinoline and piperazine-1-carboxylic acid tert-butyl ester. Crystallisation from methanol yields the title compound as a colorless solid.
MS (m/e): 348.5 (M+H$^+$)

(b) 6-Chloro-2-piperazin-1-yl-quinoline hydrochloride

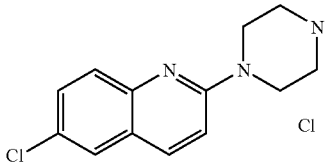

Prepared in analogy to example 1.6 (d) from 4-(6-chloro-quinolin-2-yl)-piperazine-1-carboxylic acid tert.-butyl ester and dioxane saturated with gaseous hydrochloric acid.
MS (m/e): 248.1 (M+H$^+$)

(c) [4-(6-Chloro-quinolin-2-yl)-piperazin-1-yl]-(2-isopropoxy-5-methanesulfonyl-phenyl)-methanone

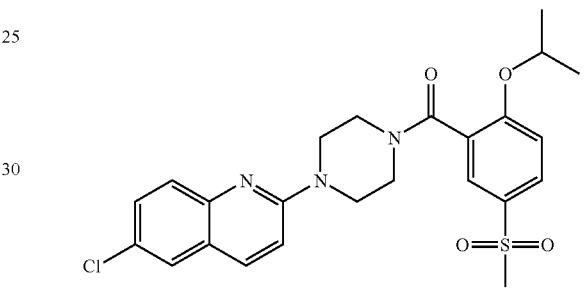

Prepared in analogy to example 1.1 (b) from 6-chloro-2-piperazin-1-yl-quinoline hydrochloride and 2-isopropoxy-5-methanesulfonyl-benzoic acid (example 2.2) in acetonitrile. Chromatography (SiO$_2$; ethyl acetate) yields the title compound as a yellowish foam.
MS (m/e): 488.1 (M+H$^+$)

EXAMPLE 1.21

Preparation of [4-(6-Chloro-quinolin-2-yl)-piperazin-1-yl]-(2-isobutoxy-5-methanesulfonyl-phenyl)-methanone

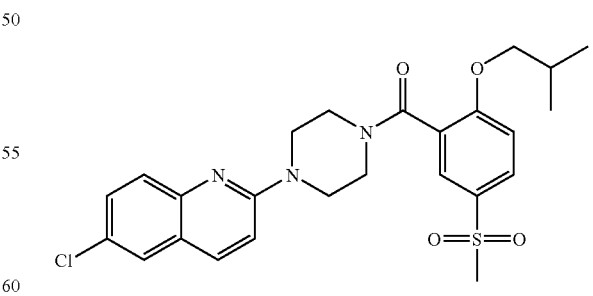

Prepared in analogy to example 1.1 (b) from 6-chloro-2-piperazin-1-yl-quinoline hydrochloride and 2-isobutoxy-5-methanesulfonyl-benzoic acid (example 2.4) in acetonitrile. Chromatography (SiO$_2$; ethyl acetate) yields the title compound as a colorless solid.
MS (m/e): 503.1 (M+H$^+$)

EXAMPLE 1.22

Preparation of [4-(6-Chloro-quinolin-2-yl)-piperazin-1-yl]-(2-cyclopentyloxy-5-methanesulfonyl-phenyl)-methanone

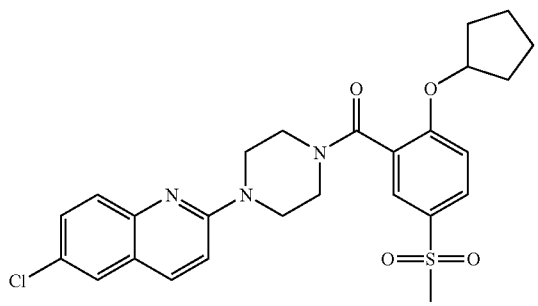

Prepared in analogy to example 1.1 (b) from 6-chloro-2-piperazin-1-yl-quinoline hydrochloride and 2-cyclopentyloxy-5-methanesulfonyl-benzoic acid (example 2.3) in acetonitrile. Chromatography (SiO$_2$; ethyl acetate) yields the title compound as a colorless solid.

MS (m/e): 515.1 (M+H$^+$)

EXAMPLE 1.23

Preparation of (2-Isobutoxy-5-methanesulfonyl-phenyl)-(4-quinoxalin-2-yl-piperazin-1-yl)-methanone (a) 4-Quinoxalin-2-yl-piperazine-1-carboxylic acid tert.-butyl ester

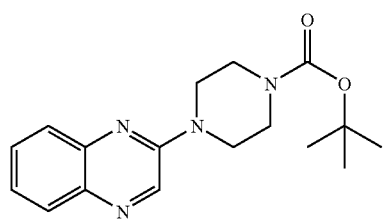

A mixture of 9.1 mmol 2-chloroquinoxaline, 10.0 mmol piperazine-1-carboxylic acid tert-butyl ester, 22.8 mmol potassium carbonate and 2.1 mmol potassium iodide in 20 ml of toluene was refluxed overnight. The reaction mixture was cooled, poured into water and extracted 3 times with ethyl acetate. The organic phase was dried, evaporated and the title compound was crystallised from methanol. Yellowish solid.

MS (m/e): 315.0 (M+H$^+$)

(b) 2-Piperazin-1-yl-quinoxaline hydrochloride

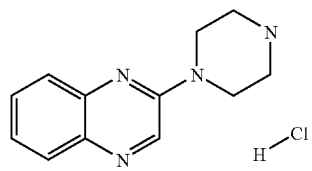

Prepared in analogy to example 1.6 (d) from 4-quinoxalin-2-yl-piperazine-1-carboxylic acid tert.-butyl ester and dioxane saturated with gaseous hydrochloric acid.

MS (m/e): 215.4 (M+H$^+$)

(c) 2-Isobutoxy-5-methanesulfonyl-phenyl)-(4-quinoxalin-2-yl-piperazin-1-yl)-methanone

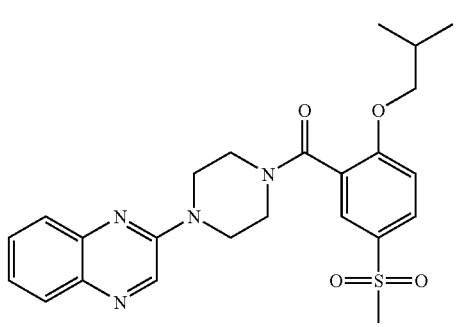

Prepared in analogy to example 1.1 (b) from 2-piperazin-1-yl-quinoxaline hydrochloride and 2-isobutoxy-5-methanesulfonyl-benzoic acid (example 2.4) in acetonitrile. Chromatography (SiO$_2$; ethyl acetate) yields the title compound as a yellowish foam.

MS (m/e): 527.3 (M+CH$_3$COO)

EXAMPLE 1.24

Preparation of (2-Isopropoxy-5-methanesulfonyl-phenyl)-(4-quinoxalin-2-yl-piperazin-1-yl)-methanone

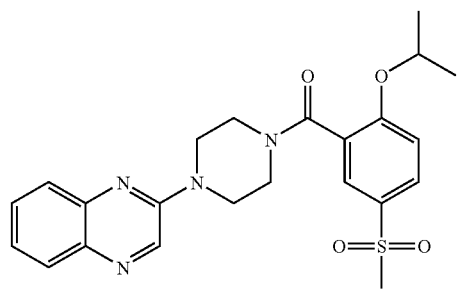

Prepared in analogy to example 1.1 (b) from 2-piperazin-1-yl-quinoxaline hydrochloride and 2-isopropoxy-5-methanesulfonyl-benzoic acid (example 2.2) in acetonitrile. Chromatography (SiO$_2$; ethyl acetate) yields the title compound as a yellowish foam.

MS (m/e): 455.5 (M+H$^+$)

EXAMPLE 1.25

Preparation of (2-Cyclopentyloxy-5-methanesulfonyl-phenyl)-(4-quinoxalin-2-yl-piperazin-1-yl)-methanone

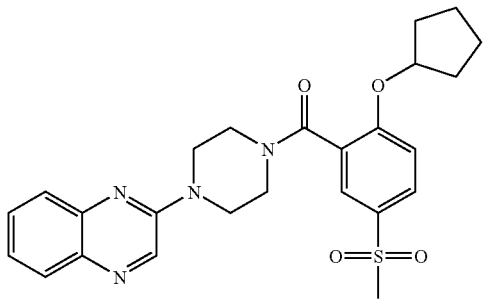

Prepared in analogy to example 1.1 (b) from 2-piperazin-1-yl-quinoxaline hydrochloride and 2-cyclopentyloxy-5-methanesulfonyl-benzoic acid (example 2.3) in acetonitrile. Chromatography (SiO$_2$; ethyl acetate) yields the title compound as a yellowish foam.

MS (m/e): 481.5 (M+H$^+$)

EXAMPLE 1.26

Preparation of (2-Isopropoxy-5-methanesulfonyl-phenyl)-(4-quinolin-3-yl-piperazin-1-yl)-methanone (a) 4-Quinolin-3-yl-piperazine-1-carboxylic acid tert.-butyl ester

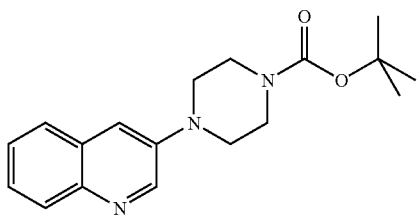

Prepared in analogy to example 1.16 (a) from 3-bromoquinoline and piperazine-1-carboxylic acid tert-butyl ester. Chromatography (SiO2; cyclohexane/ethyl acetate 1/1), followed by crystallization from diethyl ether/cyclohexane yields the title product as a colorless solid.

MS (m/e): 314.2 (M+H$^+$)

(b) 3-Piperazin-1-yl-quinoline hydrochloride

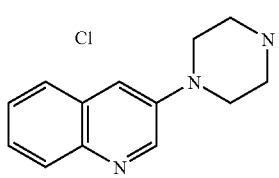

Prepared in analogy to example 1.6 (d) from 4-quinolin-3-yl-piperazine-1-carboxylic acid tert.-butyl ester and dioxane saturated with gaseous hydrochloric acid. Yellow solid.

MS (m/e): 214.4 (M+H$^+$)

(c) (2-Isopropoxy-5-methanesulfonyl-phenyl)-(4-quinolin-3-yl-piperazin-1-yl)-methanone

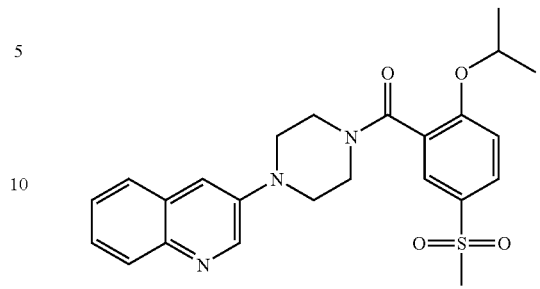

Prepared in analogy to example 1.1 (b) from 3-piperazin-1-yl-quinoline hydrochloride and 2-isopropoxy-5-methanesulfonyl-benzoic acid (example 2.2) in acetonitrile. Chromatography (SiO$_2$; ethyl acetate) yields the title compound as a colorless foam.

MS (m/e): 454.5 (M+H$^+$)

EXAMPLE 1.27

Preparation of (2-Isobutoxy-5-methanesulfonyl-phenyl)-(4-quinolin-3-yl-piperazin-1-yl)-methanone

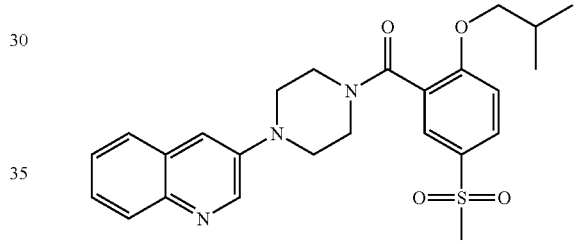

Prepared in analogy to example 1.1 (b) from 3-piperazin-1-yl-quinoline hydrochloride and 2-isobutoxy-5-methanesulfonyl-benzoic acid (example 2.4) in acetonitrile. Chromatography (SiO$_2$; ethyl acetate) yields the title compound as a colorless solid.

MS (m/e): 468.3 (M+H$^+$)

EXAMPLE 1.28

Preparation of (2-Cyclopentyloxy-5-methanesulfonyl-phenyl)-(4-quinolin-3-yl-piperazin-1-yl)-methanone

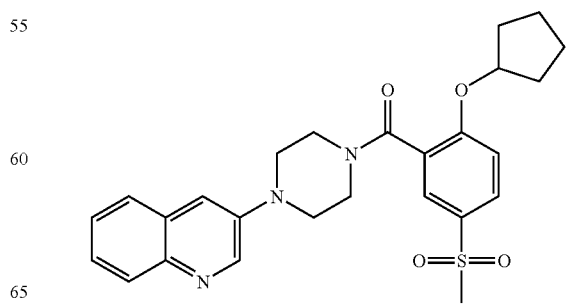

Prepared in analogy to example 1.1 (b) from 3-piperazin-1-yl-quinoline hydrochloride and 2-cyclopentyloxy-5-methanesulfonyl-benzoic acid (example 2.3) in acetonitrile. Chromatography (SiO₂; ethyl acetate) yields the title compound as a colorless solid.

MS (m/e): 480.3 (M+H⁺)

EXAMPLE 1.29

Preparation of (4-Benzo[d]isothiazol-3-yl-piperazin-1-yl)-(2-isopropoxy-5-methanesulfonyl-phenyl)-methanone

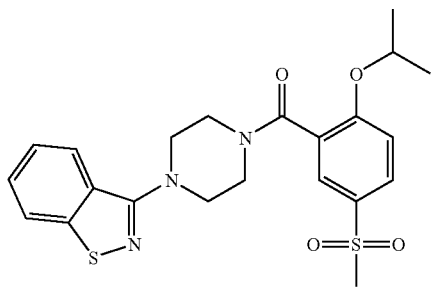

Prepared in analogy to example 1.1 b) from 2-isopropoxy-5-methanesulfonyl-benzoic acid (Example 2.2) and 3-piperazin-1-yl-benzo[d]isothiazole hydrochloride (CA=87691-88-1) in dimethylformamide. The crude material was purified by HPLC (Zorbax XDB, reversed phase, water/acetonitrile) to yield the title compound as a white foam. MS (m/e): 460.3 (M+H⁺)

EXAMPLE 1.30

Preparation of (4-Benzo[d]isothiazol-3-yl-piperazin-1-yl)-(2-diethylamino-5-methanesulfonyl-phenyl)-methanone

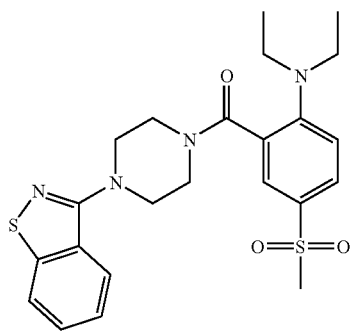

Prepared in analogy to example 1.1 b) from 2-diethylamino-5-methanesulfonyl-benzoic acid (Example 2.5) and 3-piperazin-1-yl-benzo[d]isothiazole hydrochloride (CA=87691-88-1) in acetonitrile. Chromatography (SiO₂; ethyl acetate) yields the title compound as a colorless solid. MS (m/e): 473.4 (M+H⁺; 100%)

EXAMPLE 1.31

Preparation of (4-Benzo[d]isothiazol-3-yl-piperazin-1-yl)-(2-morpholin-4-yl-5-nitro-phenyl)-methanone

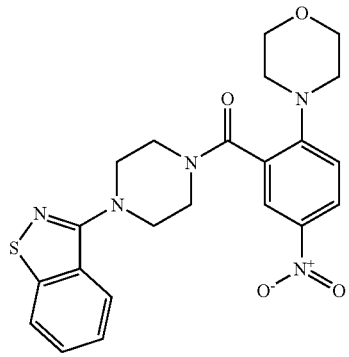

Prepared in analogy to example 1.1 b) from 2-morpholin-4-yl-5-nitro-benzoic acid (Example 2.1) and 3-piperazin-1-yl-benzo[d]isothiazole hydrochloride (CA=87691-88-1) in acetonitrile. Chromatography (SiO₂; ethyl acetate) yields the title compound as a colorless solid.

MS (m/e): 454.2 (M+H⁺; 100%)

EXAMPLE 1.32

Preparation of (4-Benzo[d]isothiazol-3-yl-piperazin-1-yl)-(2-cyclopropylmethoxy-5-methanesulfonyl-phenyl)-methanone

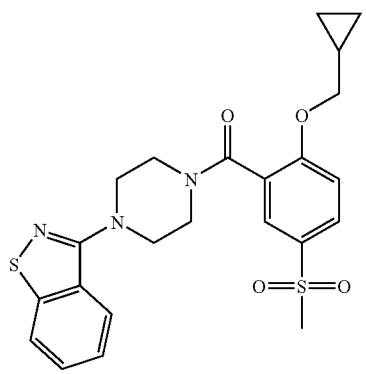

Prepared in analogy to example 1.1 b) from 2-cyclopropylmethoxy-5-methanesulfonyl-benzoic acid (Example 2.6) and 3-piperazin-1-yl-benzo[d]isothiazole hydrochloride (CA=87691-88-1) in acetonitrile. Chromatography (SiO₂; ethyl acetate) yields the title compound as a colorless solid.

MS (m/e): 472.1 (M+H⁺; 100%)

EXAMPLE 1.33

Preparation of (4-Benzo[d]isothiazol-3-yl-piperazin-1-yl)-[5-methanesulfonyl-2-((S)-2,2,2-trifluoro-1-methyl-ethoxy)-phenyl]-methanone

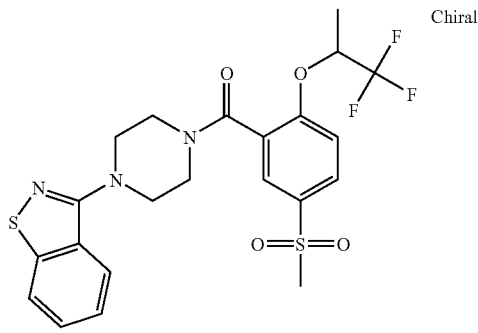

Prepared in analogy to example 1.1 b) from 5-methanesulfonyl-2-((S)-2,2,2-trifluoro-1-methyl-ethoxy)-benzoic acid (Example 2.7) and 3-piperazin-1-yl-benzo[d]isothiazole hydrochloride (CA=87691-88-1) in acetonitrile. Chromatography (SiO$_2$; ethyl acetate) yields the title compound as a colorless solid.

MS (m/e): 514.1 (M+H$^+$; 37%)

EXAMPLE 1.34

Preparation of [4-(6-Chloro-quinolin-2-yl)-piperazin-1-yl]-(2-diethylamino-5-methanesulfonyl-phenyl)-methanone

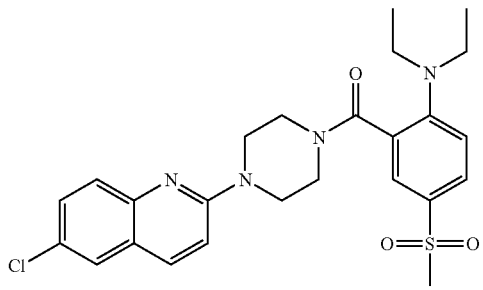

Prepared in analogy to example 1.1 b) from 6-chloro-2-piperazin-1-yl-quinoline hydrochloride (Example 1.20b) and 2-diethylamino-5-methanesulfonyl-benzoic acid (Example 2.5) in acetonitrile. Chromatography (SiO$_2$; ethyl acetate) yields the title compound as a colorless solid. MS (m/e): 501.4 (M+H$^+$; 100%)

EXAMPLE 1.35

Preparation of [4-(6-Chloro-quinolin-2-yl)-piperazin-1-yl]-(2-morpholin-4-yl-5-nitro-phenyl)-methanone

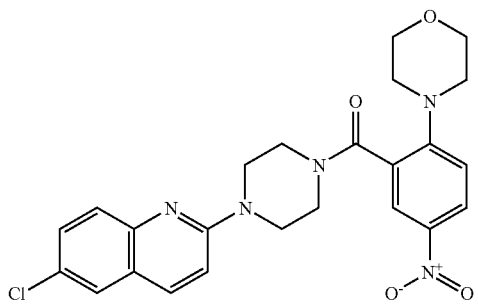

Prepared in analogy to example 1.1 b) from 6-chloro-2-piperazin-1-yl-quinoline hydrochloride (Example 1.20b) and 2-morpholin-4-yl-5-nitro-benzoic acid (Example 2.1) in acetonitrile. Chromatography (SiO$_2$; ethyl acetate) yields the title compound as a colorless solid.

MS (m/e): 482.2 (M+H$^+$; 100%)

EXAMPLE 1.36

Preparation of [4-(6-Chloro-quinolin-2-yl)-piperazin-1-yl]-[5-methanesulfonyl-2-((S)-2,2,2-trifluoro-1-methyl-ethoxy)-phenyl]-methanone

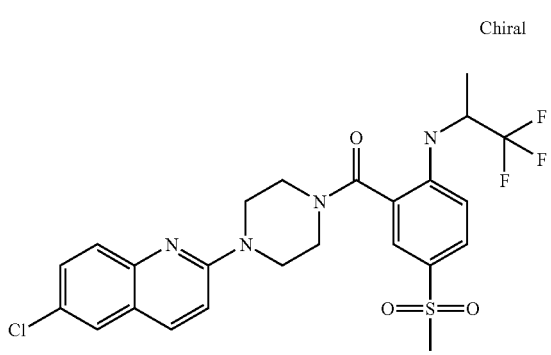

Prepared in analogy to example 1.1 b) from 6-chloro-2-piperazin-1-yl-quinoline hydrochloride (Example 1.20b) and 5-methanesulfonyl-2-((S)-2,2,2-trifluoro-1-methyl-ethoxy)-benzoic acid (Example 2.7) in acetonitrile. Chromatography (SiO$_2$; ethyl acetate) yields the title compound as a colorless solid.

MS (m/e): 542.3 (M+H$^+$; 100%)

EXAMPLE 1.37

Preparation of [4-(6-Chloro-quinolin-2-yl)-piperazin-1-yl]-(2-cyclopropylmethoxy-5-methanesulfonyl-phenyl)-methanone

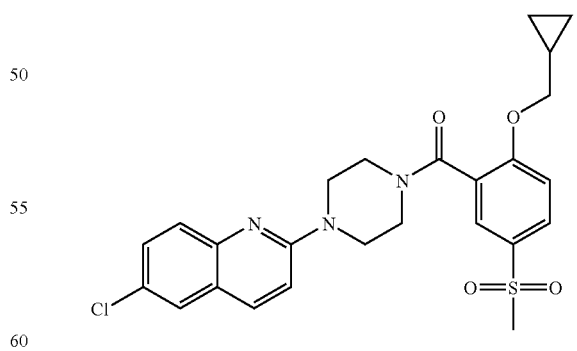

Prepared in analogy to example 1.1 b) from 6-chloro-2-piperazin-1-yl-quinoline hydrochloride (Example 1.20b) and 2-cyclopropylmethoxy-5-methanesulfonyl-benzoic acid (Example 2.6) in acetonitrile. Chromatography (SiO$_2$; ethyl acetate) yields the title compound as a colorless solid. MS (m/e): 500.3 (M+H$^+$; 100%)

EXAMPLE 1.38

Preparation of [4-(6-Chloro-benzothiazol-2-yl)-piperazin-1-yl]-(2-diethylamino-5-methanesulfonyl-phenyl)-methanone

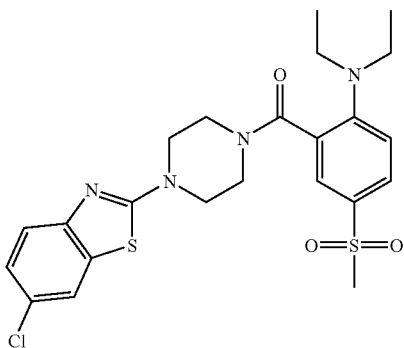

Prepared in analogy to example 1.1 b) from 5-chloro-2-piperazin-1-yl-benzothiazole (Example 1.14a) and 2-diethylamino-5-methanesulfonyl-benzoic acid (Example 2.5) in acetonitrile. Chromatography (SiO$_2$; ethyl acetate) yields the title compound as a colorless solid.

MS (m/e): 507.5 (M+H$^+$; 100%)

EXAMPLE 1.39

Preparation of [4-(6-Chloro-benzothiazol-2-yl)-piperazin-1-yl]-(2-cyclopropylmethoxy-5-methanesulfonyl-phenyl)-methanone

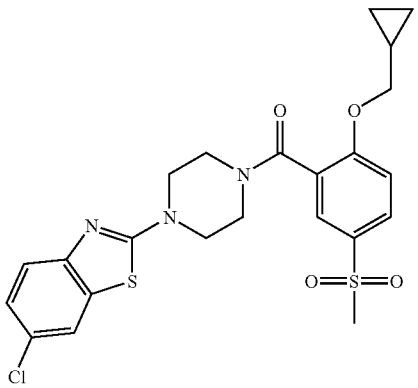

Prepared in analogy to example 1.1 b) from 5-chloro-2-piperazin-1-yl-benzothiazole (Example 1.14a) and 2-cyclopropylmethoxy-5-methanesulfonyl-benzoic acid (Example 2.6) in acetonitrile. Chromatography (SiO$_2$; ethyl acetate) yields the title compound as a colorless solid.

MS (m/e): 506.3 (M+H$^+$; 100%)

EXAMPLE 1.40

Preparation of [4-(6-Chloro-benzothiazol-2-yl)-piperazin-1-yl]-[5-methanesulfonyl-2-((S)-2,2,2-trifluoro-1-methyl-ethoxy)-phenyl]-methanone

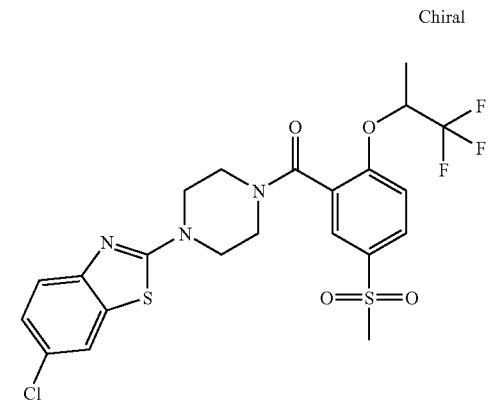

Prepared in analogy to example 1.1 b) from 5-chloro-2-piperazin-1-yl-benzothiazole (Example 1.14a) and 5-methanesulfonyl-2-((S)-2,2,2-trifluoro-1-methyl-ethoxy)-benzoic acid (Example 2.7) in acetonitrile. Chromatography (SiO$_2$; ethyl acetate) yields the title compound as a colorless solid.

MS (m/e): 548.2 (M+H$^+$; 100%)

EXAMPLE 2.1

Preparation of 2-Morpholin-4-yl-5-nitro-benzoic acid

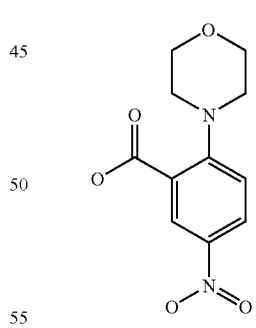

To a solution of 2-fluoro-5-nitrobenzoic acid (4.86 g, 26.2 mmol) in dioxane (50 ml) was added morpholine (11.5 ml). The mixture was stirred at room temperature for 2 hours. The solvent was removed in vacuo. The residue was dissolved in water, and the mixture was acidified with HCl 2N. The solid was filtered, washed with water and dried to provide the title compound (6.2 g, 93%) as a yellow solid, MS (m/e): 251.2 (M–H, 100%).

EXAMPLE 2.2

Preparation of
2-Isopropoxy-5-methanesulfonyl-benzoic acid (a) 2-Chloro-5-methanesulfonyl-benzoic acid

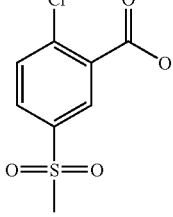

To 99 mmol 2-chloro-5-(methylthio) benzoic acid in 400 ml methanol at 0° C. 296 mmol oxone® was added, and the mixture was allowed to stir at RT for 3.5 h. The precipitate was filtered off, and the filtrate was concentrated under reduced pressure. The residue was extracted 3× with 400 ml ethyl acetate, and the combined organic phases washed 2× with 300 ml 1N HCl and with 300 ml saturated aqueous NaCl solution and dried with $MgSO_4$. Evaporation under reduced pressure yielded the title compound.

(b) 2-Isopropoxy-5-methanesulfonyl-benzoic acid

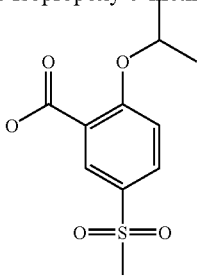

A mixture of 2.13 mmol 2-chloro-5-methanesulfonyl-benzoic acid, 0.64 mmol Cu(I)Br in 5 ml $NEt_3$ and 25 ml isopropanol was heated to 120° C. for 16 h in a sealed tube. The volatiles were removed under vacuum, and the residue was taken up in 70 ml 1N HCl. Extraction with ethyl acetate drying of the combined organic fractions, and evaporation yielded a residue which was purified by reversed phase preparative HPLC eluting with an acetonitrile/water gradient. Evaporation of the product fractions yielded the title compound
MS (m/e): 257.0 (MH⁻, 100%).

EXAMPLE 2.3

Preparation of
2-Cyclopentyloxy-5-methanesulfonyl-benzoic acid

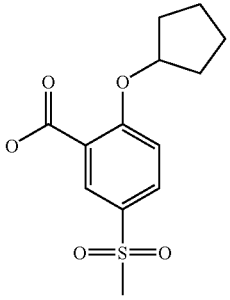

Prepared in analogy to example 2.2 (b) from 2-chloro-5-methanesulfonyl-benzoic acid and cyclopentanol.
MS (m/e): 282.9 (MH⁻, 100%)

EXAMPLE 2.4

Preparation of
2-Isobutoxy-5-methanesulfonyl-benzoic acid

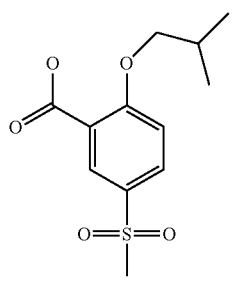

Prepared in analogy to example 2.2 (b) from from 2-chloro-5-methanesulfonyl-benzoic acid and isobutanol.
MS (m/e): 271.1 (MH⁻, 100%)

The invention claimed is:
1. A compound of formula I

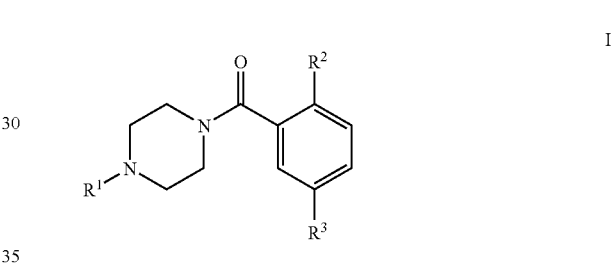

wherein
$R^1$ is the group

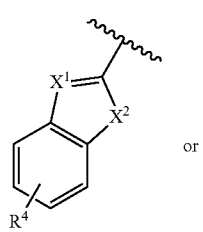

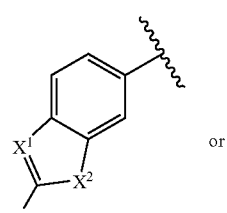

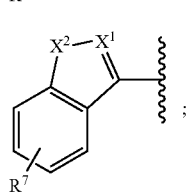

R² is morpholino, OR' or N(R")₂;
R' is lower alkyl,
  lower alkyl substituted by halogen, or
  —(CH₂)ₙ-cycloalkyl;
R" is lower alkyl;
R³ is NO₂, CN or SO₂R';
R⁴ is hydrogen, hydroxy, halogen, NO₂, lower alkyl, lower alkyl substituted by halogen, lower alkoxy, SO₂R' or C(O)OR";
R⁵, R⁶, and R⁷ are each independently hydrogen, halogen, lower alkyl or lower alkyl substituted by halogen;
X¹ is N;
X² is O or S; and
n is 0, 1 or 2;
or a pharmaceutically acceptable acid addition salt thereof.

2. A compound of claim 1 comprising formula IA

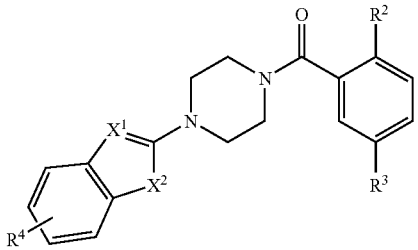

wherein
R² is morpholino, OR' or N(R")₂;
R' is lower alkyl,
  lower alkyl substituted by halogen, or
  —(CH₂)ₙ-cycloalkyl;
R" is lower alkyl;
R³ is NO₂, CN or SO₂R';
R⁴ is hydrogen, hydroxy, halogen, NO₂, lower alkyl, lower alkyl substituted by halogen, lower alkoxy, SO₂R' or C(O)OR";
X¹ is N;
X² is O or S; and
n is 0, 1 or 2;
or a pharmaceutically active acid addition salt thereof.

3. A compound of claim 2, selected from the group consisting of
[4-(6-chloro-benzothiazol-2-yl)-piperazin-1-yl]-(2-morpholin-4-yl-5-nitro-phenyl)-methanone,
[4-(6-chloro-benzothiazol-2-yl)-piperazin-1-yl]-(2-isopropoxy-5-methanesulfonyl-phenyl)-methanone,
(4-benzooxazol-2-yl-piperazin-1-yl)-(2-cyclopentyloxy-5-methanesulfonyl-phenyl)-methanone,
(4-benzooxazol-2-yl-piperazin-1-yl)-(2-isobutoxy-5-methanesulfonyl-phenyl)-methanone,
(2-isopropoxy-5-methanesulfonyl-phenyl)-[4-(6-methoxy-benzothiazol-2-yl)-piperazin-1-yl]-methanone,
(2-isopropoxy-5-methanesulfonyl-phenyl)-[4-(6-nitro-benzothiazol-2-yl)-piperazin-1-yl]-methanone, and
(2-isopropoxy-5-methanesulfonyl-phenyl)-[4-(4-methoxy-benzothiazol-2-yl)-piperazin-1-yl]-methanone.

4. A compound of claim 2, selected from the group consisting of
(2-isopropoxy-5-methanesulfonyl-phenyl)-[4-(4-nitro-benzothiazol-2-yl)-piperazin-1-yl]-methanone,
[4-(4-hydroxy-benzothiazol-2-yl)-piperazin-1-yl]-(2-isopropoxy-5-methanesulfonyl-phenyl)-methanone,
[4-(5-chloro-benzothiazol-2-yl)-piperazin-1-yl]-(2-isopropoxy-5-methanesulfonyl-phenyl)-methanone,
[4-(6-ethoxy-benzothiazol-2-yl)-piperazin-1-yl]-(2-isopropoxy-5-methanesulfonyl-phenyl)-methanone,
[4-(6-chloro-benzothiazol-2-yl)-piperazin-1-yl]-(2-cyclopropylmethoxy-5-methanesulfonyl-phenyl)-methanone and
[4-(6-chloro-benzothiazol-2-yl)-piperazin-1-yl]-[5-methanesulfonyl-2-((S)-2,2,2-trifluoro-1-methyl-ethoxy)-phenyl]-methanone.

5. A compound of claim 1 comprising formula IB

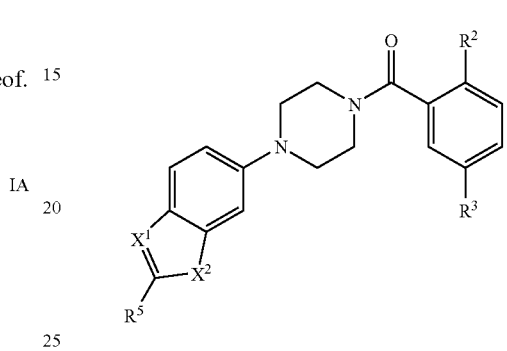

wherein
R² is morpholino, OR' or N(R")₂;
R' is lower alkyl,
  lower alkyl substituted by halogen, or
  —(CH₂)ₙ-cycloalkyl;
R" is lower alkyl;
R³ is NO₂, CN or SO₂R';
R⁵ is hydrogen, halogen, lower alkyl or lower alkyl substituted by halogen;
X¹ is N;
X² is O or S; and
n is 0, 1 or 2;
or a pharmaceutically acceptable acid addition salt thereof.

6. A compound of claim 5, which is
(2-isobutoxy-5-methanesulfonyl-phenyl)-[4-(2-methyl-benzothiazol-5-yl)-piperazin-1-yl]-methanone.

7. A compound of claim 1 comprising formula ID

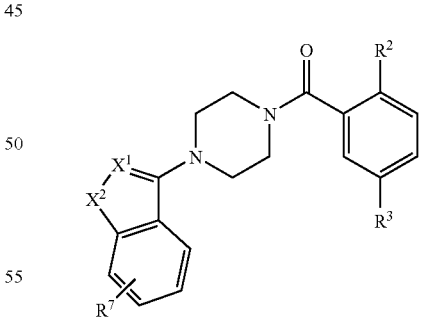

wherein
R² is morpholino, OR' or N(R")₂;
R' is lower alkyl,
  lower alkyl substituted by halogen, or
  —(CH₂)ₙ-cycloalkyl;
R" is lower alkyl;
R³ is NO₂, CN or SO₂R';
R⁷ is hydrogen, halogen, lower alkyl or lower alkyl substituted by halogen;

$X^1$ is N;
$X^2$ is O or S; and
n is 0, 1 or 2;
or a pharmaceutically acceptable acid addition salt thereof.

8. A compound of claim 7, selected from the group consisting of
(4-benzo[d]isothiazol-3-yl-piperazin-1-yl)-(2-isopropoxy-5-methanesulfonyl-phenyl)-methanone,
(4-benzo[d]isothiazol-3-yl-piperazin-1-yl)-(2-cyclopropyl-methoxy-5-methanesulfonyl-phenyl)-methanone and
(4-benzo[d]isothiazol-3-yl-piperazin-1-yl)-[5-methane-sulfonyl-2-((S)-2,2,2-trifluoro-1-methyl-ethoxy)-phenyl]-methanone.

9. A pharmaceutical composition comprising a therapeutic amount of a compound of formula I

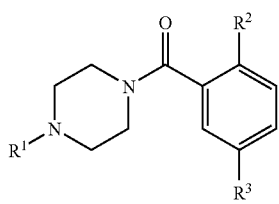

I wherein
$R^1$ is the group

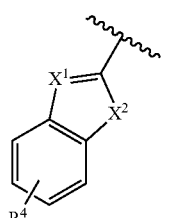

A or

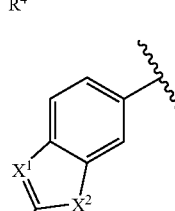

B or

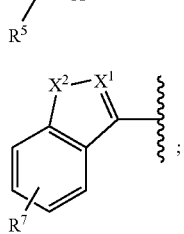

D

;

$R^2$ is morpholino, OR' or N(R")$_2$;
R' is lower alkyl,
   lower alkyl substituted by halogen, or
   —(CH$_2$)$_n$-cycloalkyl;
R" is lower alkyl;
$R^3$ is NO$_2$, CN or SO$_2$R';
$R^4$ is hydrogen, hydroxy, halogen, NO$_2$, lower alkyl, lower alkyl substituted by halogen, lower alkoxy, SO$_2$R' or C(O)OR";
$R^5$, $R^6$, and $R^7$ are each independently hydrogen, halogen, lower alkyl or lower alkyl substituted by halogen;
$X^1$ is N;
$X^2$ is O or S; and
n is 0, 1 or 2;
or a pharmaceutically acceptable acid addition salt thereof and a pharmaceutically acceptable carrier.

10. A process for preparing a compound of formula I

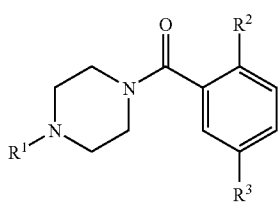

I wherein
$R^1$ is the group

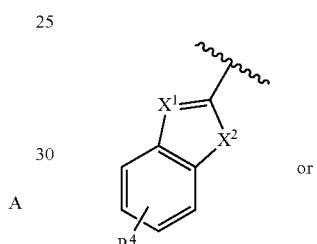

A or

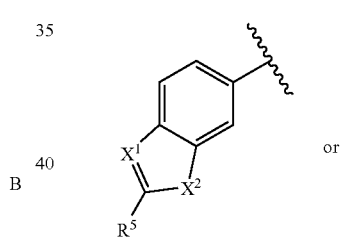

B or

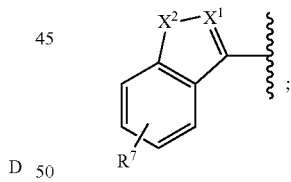
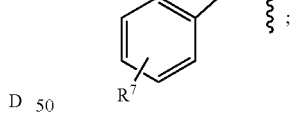

D

;

$R^2$ is morpholino, OR' or N(R")$_2$;
R' is lower alkyl,
   lower alkyl substituted by halogen, or
   —(CH$_2$)$_n$-cycloalkyl;
R" is lower alkyl;
$R^3$ is NO$_2$, CN or SO$_2$R';
$R^4$ is hydrogen, hydroxy, halogen, NO$_2$, lower alkyl, lower alkyl substituted by halogen, lower alkoxy, SO$_2$R' or C(O)OR";
$R^5$, $R^6$, and $R^7$ are each independently hydrogen, halogen, lower alkyl or lower alkyl substituted by halogen;
$X^1$ is N;
$X^2$ is O or S; and
n is 0, 1 or 2;

wherein the process is selected from the group consisting of
a) reacting a compound of formula

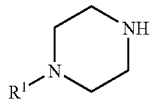   II with a compound of formula

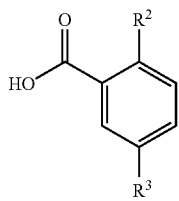   III in the presence of an activating agent
to produce a compound of formula

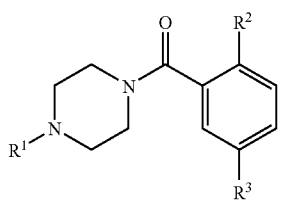   I b) reacting a compound of formula

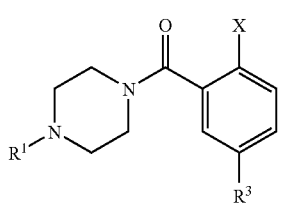   IV with a compound of formula

R₂H   V in the presence of a base or with addition of a catalyst
to produce a compound of formula

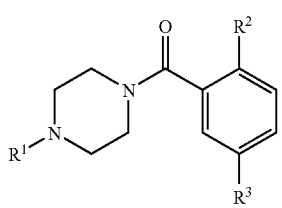   I wherein X is halogen;

c) reacting a compound of formula

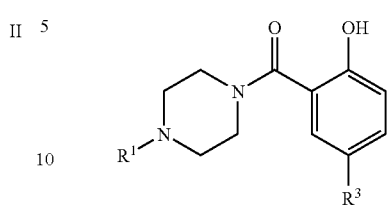   I1 with a compound of formula

R'X   VI to produce a compound of formula

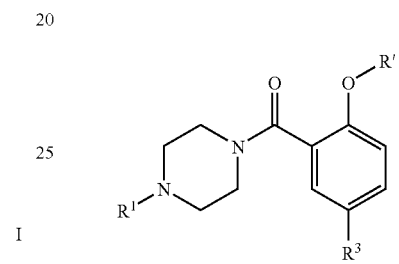   I2 wherein X is halogen; and
d) reacting a compound of formula

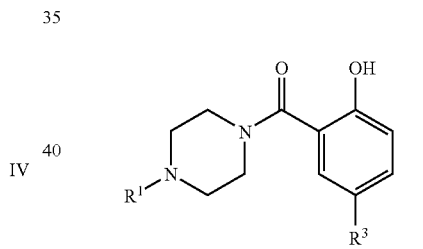   I1 with a compound of formula

R'OH   VII under Mitsunobu conditions
to produce a compound of formula

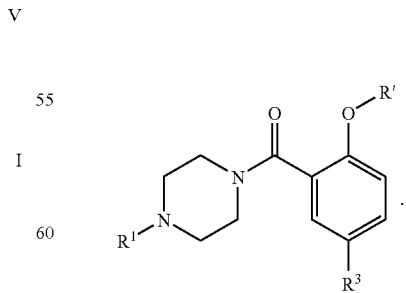   I2

.

11. A method of treating schizophrenia comprising administering to an individual a therapeutically effective amount of a compound of formula I

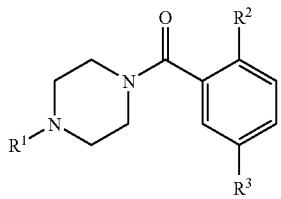

wherein
R¹ is the group

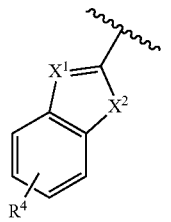

or

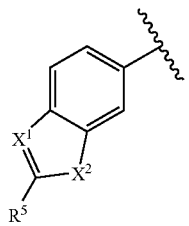

or

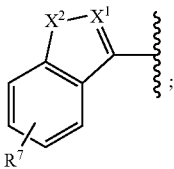

;

R² is morpholino, OR' or N(R")₂;
R' is lower alkyl,
    lower alkyl substituted by halogen, or
    —(CH₂)$_n$-cycloalkyl;
R" is lower alkyl;
R³ is NO₂, CN or SO₂R';
R⁴ is hydrogen, hydroxy, halogen, NO₂, lower alkyl, lower alkyl substituted by halogen, lower alkoxy, SO₂R' or C(O)OR";
R⁵, R⁶, and R⁷ are each independently hydrogen, halogen, lower alkyl or lower alkyl substituted by halogen;
X¹ is N;
X² is O or S; and
n is 0, 1 or 2;
or a pharmaceutically acceptable acid addition salt thereof.

* * * * *